(12) United States Patent
Read et al.

(10) Patent No.: US 7,378,535 B2
(45) Date of Patent: May 27, 2008

(54) PRODUCTION OF FURANONES

(75) Inventors: Roger Read, Kensington (AU); Naresh Kumar, Maroubra (AU)

(73) Assignee: Unisearch Limited, A.C.N., Sydney (AU)

( * ) Notice: Subject to any disclaimer, the term of this patent is extended or adjusted under 35 U.S.C. 154(b) by 0 days.

(21) Appl. No.: 11/414,552

(22) Filed: May 1, 2006

(65) Prior Publication Data
US 2007/0032666 A1 Feb. 8, 2007

Related U.S. Application Data

(63) Continuation-in-part of application No. 09/673,305, filed as application No. PCT/AU99/00285 on Apr. 16, 1999, now Pat. No. 7,064,220.

(30) Foreign Application Priority Data
Apr. 16, 1998 (AU) .................... PP 2978

(51) Int. Cl.
C07D 307/58 (2006.01)
(52) U.S. Cl. .................... 549/313
(58) Field of Classification Search ................. 549/313
See application file for complete search history.

(56) References Cited
U.S. PATENT DOCUMENTS
6,635,692 B1 10/2003 Christie et al. ............. 523/122

2004/0072898 A1 4/2004 Kjelleberg et al. .......... 514/473

FOREIGN PATENT DOCUMENTS
WO  WO 96/29392  9/1996

OTHER PUBLICATIONS

Kjelleberg et al. (1996) Methods for Microbial Regulation, Chemical Abstract 126:4540.
Manny at al. (1997) Reinvestigation of the Sulfuric Acid-Catalyzed Cyclization of Brominated 2-alkyllevulinic Acids to 3-Alkyl-5-Methylene-2(5H)-Furanones, Chemical Abstract 128:34643.
Kotsuki et al. (1983) Efficient Synthesis of Acetoxyfimbrolides and Beckerelides Analogs, Chem. Lett. pp. 1007-1008.
Cueto et al. (1997) New Acetyl Derivatives from Antartic *Delisea fimbriata*, J. Nat. Prod. 60:279-281.
Manny et al. (1997) Reinvestigation of the Sulfuric Acid-Catalysed Cyclisation of Brominated 2-Alkyllevulinic Acids to 3-Alkyl-5-Methylene-2(5H)-Furanones, Tetrahedron 53(46):15813-15826.

*Primary Examiner*—Taylor Victor Oh
(74) *Attorney, Agent, or Firm*—Morgan, Lewis & Bockius LLP

(57) ABSTRACT

The present invention relates to the side chain functionalization of fimbrolides (halogenated 3-alkyl-5-methylene-2 (5H)-furanones) and their synthetic analogues, that yields fimbrolides substituted with a halogen, an oxygen or a nitrogen functionality in the alkyl chain, especially fimbrolide alcohols, carboxylate and sulfinate and sulfonate esters, ethers, aldehydes, ketones, acids, amides, nitro derivatives, hydrophobic, hydrophilic and fluorophilic alkyl derivatives and polymers.

3 Claims, 14 Drawing Sheets

| Compound | Structure |
|---|---|
| 3 (d5) | 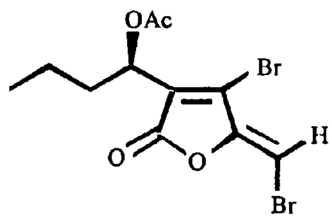 |
| 4 (d19) | 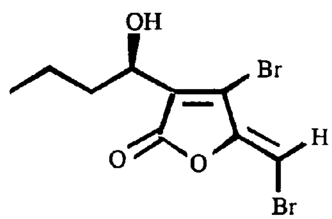 |
| 5 (d14) | 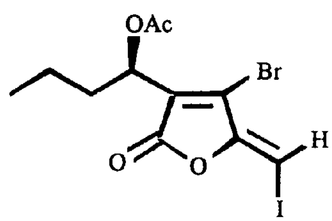 |

PRODUCTION OF FURANONES

CROSS REFERENCE TO RELATED APPLICATIONS

This application is a continuation-in-part of U.S. application Ser. No. 09/673,305, filed Mar. 19, 2001 now U.S. Pat. No. 7,064,220, which is a U.S. National Phase application of International Application PCT/AU99/00285, filed Apr. 16, 1999, which claims the benefit of priority of Australian Patent Application No. PP2978, filed Apr. 16, 1998, all of which are herein incorporated by reference in their entirety.

TECHNICAL FIELD

The present invention relates to the side chain functionalisation of fimbrolides (halogenated 3-alkyl-5-methylene-2(5H)-furanones) and their synthetic analogues, that yields fimbrolides substituted with a halogen, an oxygen or a nitrogen functionality in the alkyl chain, especially fimbrolide alcohols, carboxylate and sulfinate and sulfonate esters, ethers, aldehydes, ketones, acids, amides, nitro derivatives, and polymers.

BACKGROUND ART

It is known that a variety of fimbrolides possessing antifungal and antimicrobial properties can be isolated from red marine algae *Delisea fimbriata, Delisea elegans* and *Delisea pulchra*. The very few reported syntheses of functionalised fimbrolides use (E)-β-bromo-β-lithioacrylate or 3-formyl-6-methylfuran or allenes as starting materials. These syntheses are unnecessarily long, tedious and give very low yields of the fimbrolides. The present inventors have recently reported the preparation of a range of fimbrolides having different sized chain lengths (Manny et al (1997) Tetrahedron 53: 15813-15826, the disclosure of which is incorporated herein by reference).

Prior to the present invention, it had not been appreciated that the side chains of the fimbrolides could be functionalised directly affording a variety of halogen or oxygen functionalised fimbrolides. We have found that fimbrolides behave like allylic or benzylic compounds in their reactivity and consequently are amenable to free radical functionalisation. The derived halogen compounds can be converted to alcohols or to esters directly from the halogen derivatives or to ketones, esters, amides, alcohols or other halides indirectly from the corresponding esters or alcohols. The fimbrolides substituted with an appropriate group in the alkyl chain are capable of yielding polymers through that group, either directly or via copolymerisation with suitable monomers. It is the preparation of these fimbrolide-based halides, alcohols, esters, ethers, amines, amides, and nitro compounds, ketones, oligomers and polymers that form the major aspect of this invention.

The fimbrolides prepared in accordance with the present invention include not only synthetic versions of the two naturally occurring fimbrolides, but also other functionalised fimbrolides which we believe to be novel compounds. The compounds synthesised in accordance with the present invention may be according to formula (I):

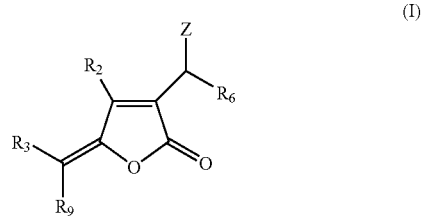

wherein $R_6$ is H, OH, alkyl, alkoxy, oxoalkyl, alkenyl, aryl or arylalkyl whether unsubstituted or substituted, straight chain or branched chain, hydrophobic, hydrophilic or fluorophilic;

$R_2$ and $R_3$ are independently or both H or halogen;

$R_9$ is halogen;

Z is independently selected from the group $R_6$, halogen, OOH, OC(O)$R_6$, =O, amine, azide, thiol, $R_6$, mercaptoalkyl, alkenyloxy, mercaptoalkenyl, aryloxy, mercaptoaryl, arylalkyloxy, mercaptoarylalkyl, SC(O)$R_6$, OS(O)$R_6$, OS(O)$_2R_6$, NHC(O)$R_6$=NR$_4$ or NHR$_4$; and $R_4$ is OH, alkyl, alkoxy, poly(ethylene glycol), alkenyl, aryl or arylalkyl.

Compounds according to Formula (I), apart from those in which $R_1$=propyl, $R_2$=Br, $R_3$=H, $R_9$=Br and Z is OC(O)CH$_3$ or OH, are believed to be novel and form part of the present invention.

DISCLOSURE OF INVENTION

In a first aspect, the present invention provides a method to form a fimbrolide derivative, the method including reacting a fimbrolide with a halogenating agent and/or an oxygenating agent to form compounds with formula (Ia):

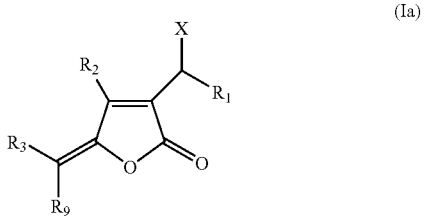

wherein $R_1$ is hydrogen, alkyl, alkoxy, oxoalkyl, alkenyl, aryl or arylalkyl, whether unsubstituted or substituted, straight chain or branched chain, hydrophobic, hydrophilic or fluorophilic;

X is halogen (X=F, Cl, Br or I), OH, OOH, OC(O)$R_1$ or =O);

$R_2$ and $R_3$ are independently or both hydrogen or halogen; and $R_9$ is halogen.

The fimbrolide used in the method may be a fimbrolide having the formula:

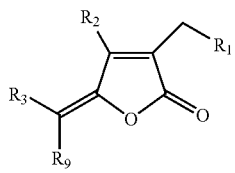

wherein $R_1$, $R_2$, $R_3$ and $R_9$ are as defined above.

Moreover, the fimbrolide of the present invention may have the following formula:

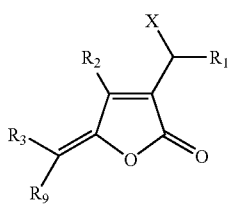

(Ia)

wherein $R_1$ is hydrogen, alkyl, alkoxy, oxoalkyl, alkenyl, aryl or arylalkyl;

X is halogen, OH, OC(O)$R_1$, alkoxy, alkenyloxy, aryloxy, or arylalkyloxy;

$R_2$ is hydrogen;

$R_3$ and $R_9$ are each halogen; and wherein each substituent can be substituted or unsubstituted, straight chain or branched chain; and provided that the compound is not

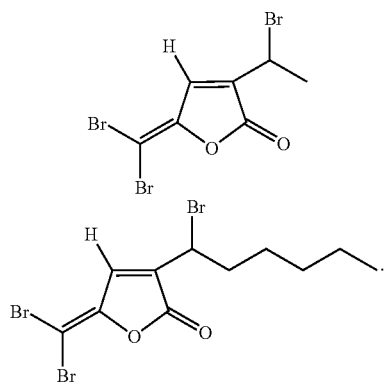

In one embodiment, X is F, Cl, 1, OH, OC(O)$R_1$, alkoxy, alkenyloxy, aryloxy, or arylalkyloxy. In another embodiment, X is OH, OC(O)$R_1$, alkoxy, alkenyloxy, aryloxy, or arylalkyloxy.

Preferably the halogenating agent is selected from N-bromosuccinimide, N-chlorosuccinimide, N-iodosuccinimide, bromine, cupric bromide, and phenyltrimethylammonium perbromide. It will be appreciated, however, that other halogenating agents would also be suitable for the present invention.

Preferably the oxygenating agent is selected from lead tetraacetate, Rose Bengal/oxygen gas, hydrogen peroxide/ vanadium pentoxide, selenium dioxide, and 3-chloroperoxybenzoic acid. It will be appreciated, however, that other oxygenating agents would also be suitable for the present invention.

The reaction conditions are selected so as to be appropriate to the nature of the reaction being undertaken. Preferably, the reaction conditions when an halogenating agent is used are for example carbon tetrachloride or chloroform or dichloromethance/with or without light/reflux, tetrahydrofuran/room temperature.

Preferably, the reaction conditions when an oxygenating agent is used are acetic acid or acetic acid mixed with a solvent/reflux, pyridine/room temperature, acetone/30° C., dioxane/reflux, and dichloromethane/room temperature.

The present inventors have found that the preferred bromination conditions are N-bromosuccinimide in the presence of catalytic amounts of benzoyl peroxide in carbon tetrachloride and light/reflux. The source of light may be any suitable source for example, the present inventors have found that a 250 W sun lamp is quite suitable.

In a second aspect, the present invention consists in a fimbrolide derivative having formula (Ia), wherein $R_1$ is hydrogen, alkyl, alkoxy, oxoalkyl, alkenyl, aryl or arylalkyl whether unsubstituted or substituted, straight chain or branched chain, hydrophobic, hydrophilic or fluorophilic; X is halogen (X=Cl, Br or I) or oxygen (X=OH, OOH, OC(O)$R_1$ or =O); $R_2$, $R_3$ are independently or both hydrogen or halogen and; $R_9$ is halogen, with the proviso that the following two derivatives are excluded $R_1$=propyl, X=OH, $R_2$=Br, $R_3$=H; and $R_1$=propyl, X=OC(O)CH$_3$, $R_2$=Br, $R_3$=H).

In a third aspect, the present invention consists of a method to form a fimbrolide derivative, the method including displacement and/or functionalisation of the halogen or oxygen substituent in the fimbrolide side chain by treating with a nucleophile or an electrophile to form compounds with formula (II):

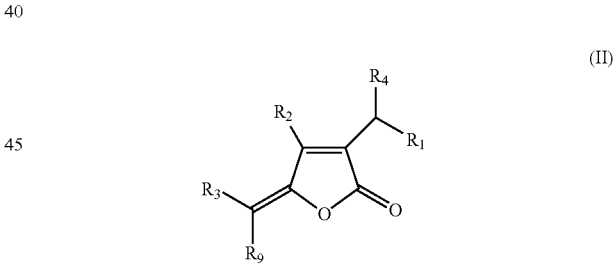

(II)

wherein $R_1$ is hydrogen, alkyl, alkoxy, oxoalkyl, alkenyl, aryl or arylalkyl, whether unsubstituted or substituted, straight chain or branched chain, hydrophobic, hydrophilic or fluorophilic;

$R_2$ and $R_3$ are independently or both hydrogen or halogen;

$R_9$ is halogen; and $R_4$ is selected from the group halogen, amine, azide, hydroxyl, thiol, or any hydrophobic, hydrophilic of fluorophilic alkyl, alkoxy, mercaptoalkyl, alkenyloxy, mercaptoalkenyl, aryloxy, mercaptoaryl, arylalkyloxy, mercaptoarylalkyl, OC(O)$R_1$, SC(O)$R_1$, OS(O)$R_1$, OS(O)$_2R_1$, NHC(O)$R_1$, OC(O)NHR$_1$, or =O.

The fimbrolide treated in the method of the third aspect may be compound of the formula:

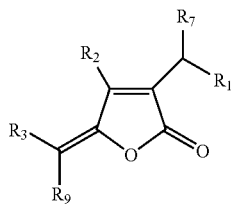

wherein $R_1$, $R_2$, $R_3$ and $R_9$ are as defined above and $R_7$ is halogen (F, Cl, Br or I), OH, OOH, OC(O)$R_1$, or =O);

Preferably the nucleophile is selected from metal halides, water, organic metal carboxylates, organic alcohols, dimethyl sulfoxide, and organonitriles. It will be appreciated, however, that other nucleophiles would also be suitable for the present invention.

Preferably the electrophile is selected from organic acids, isocyanates, carboxylic or sulfonic acid halides or active acylating or sulfinylating agents such as carbonyl imidazoles, carboxylic anhydrides, carbodiimide activated carboxylic acids, sulfonyl halides, and sulfonic anhydrides and diethylaminosulfur trifluoride. It will be appreciated, however, that other electrophiles would also be suitable for the present invention.

The reaction conditions of the method of the third aspect are selected to be appropriate to the nature of the reaction being undertaken.

The reaction conditions suitable when using a nucleophile are acetone or dioxane/room temperature or reflux, water/dioxane or acetone or tetrahydrofuran/reflux, metal acetates/organic acids/neat or high boiling solvents/reflux, organic alcohols/reflux, dimethyl sulfoxide/room temperature, and organonitriles/acid catalyst or silver triflate/reflux.

The reaction conditions suitable when using an electrophile are organic acids/neat and/or solvent/acid catalyst/reflux, organic acid halides or anhydrides or isocyanates/base catalyst/solvent/room temperature, and diethylaminosulfur trifluoride/dichloromethane/low temperature.

In a fourth aspect the present invention consists in a fimbrolide derivative having formula (II), wherein $R_1$ is hydrogen, alkyl, alkoxy, oxoalkyl, alkenyl, aryl or arylalkyl whether unsubstituted or substituted, straight chain or branched chain, hydrophobic, hydrophilic or fluorophilic; $R_2$ and $R_3$ are independently or both hydrogen or halogen; $R_9$ is halogen, and $R_4$ is selected from the group halogen, amine, azide, hydroxyl, thiol, or any hydrophobic, hydrophilic or fluorophilic alkyl, alkoxy, mercaptoalkyl, alkenyloxy, mercaptoalkenyl, aryloxy, mercaptoaryl, arylalkyloxy, mercaptoarylalky, OC(O)$R_1$, SC(O)$R_1$, OS(O)$R_1$, OS(O)$_2$$R_1$, NHC(O)$R_1$, OC(O)NHR$_1$, or =O, with the proviso that the following two derivatives are excluded $R_1$=propyl, X=OH, $R_2$=Br, $R_3$=H; 2. $R_1$=propyl, X=OC(O)CH$_3$, $R_2$=Br, $R_3$=H.

In a fifth aspect, the present invention consists of a method to form a fimbrolide derivative the method including reacting an hydroxyl substituent in the fimbrolide side chain with an oxidising agent to form a compound in accordance with formula (III):

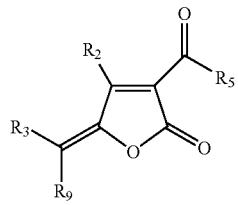

wherein $R_2$ and $R_3$ are independently or both hydrogen or halogen;

$R_5$ is OH or the same as $R_1$;

$R_9$ is halogen; and $R_1$ is hydrogen, alkyl, alkoxy, oxoalkyl, alkenyl, aryl or arylalkyl whether unsubstituted or substituted, straight chain or branched chain, hydrophobic, hydrophilic or fluorophilic.

The hydroxyl substituted fimbrolide used in the method of the fifth aspect may have the formula:

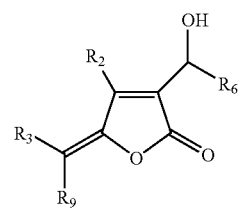

wherein $R_5$, $R_2$ and $R_3$ are as defined above.

Preferably, the oxidising agents are acidic chromium reagents in any form either free or polymer supported (e.g. Jones reagent, pyridinium chlorochromate, pyridinium dichromate, chromium trioxide etc), manganese dioxide, potassium permanganate, selenium dioxide, ceric ammonium nitrate, ruthenium tetraoxide, and hot nitric acid. It will be appreciated, however, that other oxidation agents may also be used for the present invention.

The reaction condition under which the method of the third aspect is performed may be any suitable conditions. The reaction conditions preferably use Jones reagent/with or without phase transfer catalysts/acetone/room temperature, toluene/reflux, potassium permanganate/buffered solution/room temperature, dioxane/reflux, ceric ammonium nitrate/aqueous acetic acid/steam bath, carbon tetrachloride/reflux, and acetic acid/steam bath. It will be appreciated, however, that other reaction conditions may also be used for the present invention.

The present inventors have found that the use of Jones reagent in acetone/room temperature is particularly suitable.

In a sixth aspect, the present invention consists in a fimbrolide derivative having the formula (III) wherein $R_1$ is hydrogen, alkyl, alkoxy, oxoalkyl, alkenyl, aryl or arylalkyl whether unsubstituted or substituted, straight chain or branched chain, hydrophobic, hydrophilic or fluorophilic; $R_2$ and $R_3$ are independently or both hydrogen or halogen; $R_9$ is halogen; and $R_5$ is OH or the same as $R_1$.

The present invention also provides a method for forming fimbrolide oximes, imines, hydrazones and amines.

Accordingly in a seventh aspect, the present invention consists of a method to form a fimbrolide analogue derived from a compound of formula (III), the method including reacting an aldehyde or ketone substituent in the fimbrolide side chain of the compound with an amine derivative to form a compound with formula (IV) or (V):

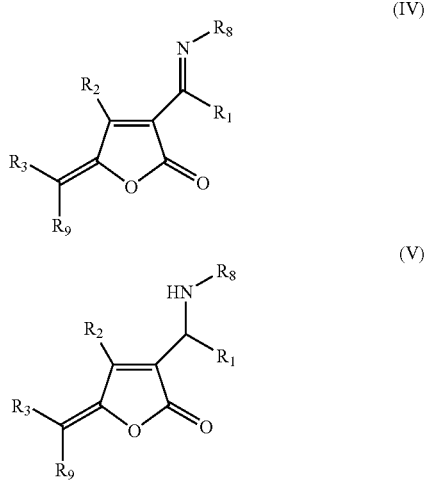

wherein $R_1$ is hydrogen, alkyl, alkoxy, oxoalkyl, alkenyl, aryl or arylalkyl whether unsubstituted or substituted, straight chain or branched chain, hydrophobic, hydrophilic or fluorophilic;

$R_2$ and $R_3$ are independently or both hydrogen or halogen;

$R_9$ is halogen and $R_8$ is OH, $NHR_1$, $NHC(X)NH_2$, $NHC(X)NHR_1$, (X=O, S, $NR_1$) or any $R_1$.

Preferably, the amine derivatives used are hydroxyl amine hydrochloride, alkyl and aryl hydrazines, alkyl or aryl amine in the presence or absence of a reducing agent. It will be appreciated, however, that other amine derivatives may also be used for the present invention.

The reaction conditions used in the method of the seventh aspect may be any conditions suitable for the nature of the reaction carried out. For example when using an amine derivative suitable conditions are ethanol or methanol/room temperature or reflux, toluene in the presence of a catalyst/ room temperature or reflux and ethanol or methanol in the presence of sodium borohydride or sodium cyanoborohydride/room temperature or reflux.

In an eighth aspect, the present invention consists in a fimbrolide derivative having the formula (IV) and (V) wherein $R_1$ is hydrogen, alkyl, alkoxy, oxoalkyl, alkenyl, aryl or arylalkyl whether unsubstituted or substituted, straight chain or branched chain, hydrophobic, hydrophilic or fluorophilic; $R_2$ and $R_3$ are independently or both hydrogen or halogen; $R_9$ is halogen and $R_8$ is OH, $NHR_1$, $NHC(X)NH_2$, $NHC(X)NHR_1$ (X=O, S, $NR_1$) or any $R_1$.

In a ninth aspect, the present invention provides an oligomer or polymer formed by oligomerising or polymerising a compound in accordance with the present invention directly or with one or more other monomers.

The one or more other monomer may be any suitable polymerisable copolymer eg acrylate ester such as alkyl, hydroxyalkyl, aminoalkyl, or substituted aryl, acrylates or methacrylates, crotonates, substituted or unsubstituted acrylonitriles, vinyl alcohols or acetates, and styrene.

In a tenth aspect, the present invention consists in incorporation of fimbrolides according to the first, third, fifth or seventh aspects of the present invention either in surface coatings or polymers through the newly introduced functionality on the alkyl chain or the alkyl chain itself via direct polymerisation or copolymerisation with suitable monomers.

In a eleventh aspect, the present invention consists in a fimbrolide derivative produced by the method according to the first, third, fifth or seventh aspects of the present invention.

In an twelfth aspect, the present invention consists in the use of a fimbrolide derivative according to the present invention. The present inventors have found that many of the fimbrolide derivatives having the formula (I), have antimicrobial, antiseptic, microbacterial static and/or antifouling properties. Accordingly, the fimbrolide derivatives are suitable for use as antimicrobial and/or antifouling agents.

In a thirteenth aspect the present invention provides a compound of formula (VI):

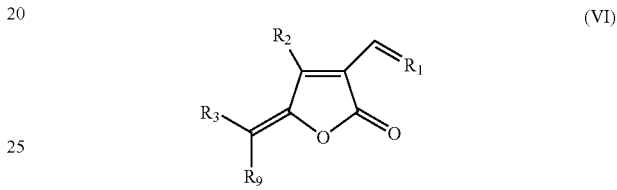

wherein $R_2$, $R_3$, $R_9$ and $R_1$ (except where $R_1$ is hydrogen) are as defined above.

An example of a compound in accordance with this form of the invention is 4-Bromo-5-(bromomethylene)-3(-1-butenyl)-2(5H)-furanone.

The compound of the thirteenth aspect may be formed by dehydrating hydroxyl substituent in the fimbrolide side chain. The dehydration may be catalysed by $H_2SO_4$ in the presence of toluene.

As used herein and in the claims:

The term "halogen" means F, Cl, Br, or I.

The term "alkyl" is taken to mean straight chain, branched chain and cyclic alkyl or cycloalkyl groups such as methyl, ethyl, propyl, isopropyl, butyl, isobutyl, sec-butyl, tert-butyl, pentyl, cyclopentyl, hexyl, cyclohexyl, and the like. Preferably the alkyl group is of 1-25 carbon atoms. The alkyl group may be optionally substituted by one or more of fluorine, chlorine, bromine, iodine, carboxyl, $C_1$-$C_4$-alkoxycarbonyl, hydroxyl, carbonyl and aryl groups.

The term "aryl" is taken to include substituted and unsubstituted phenyl, napthyl or other benzenoid aromatic or any aromatic heterocyclic nucleus containing N, O, S, P or chalcogen heteroatom such as pyridyl, pyrimidyl, indolyl or furanyl.

The term "alkoxy" as used herein and in the claims denotes straight chain or branched alkoxy, preferably containing 1 to 25 carbon atoms and like functional groups, such as polyethylene glycol (PEG) and cyclic ethers.

The term "alkenyl" is taken to mean a straight chain, a branched chain or cycloalkyl group having one or more double bonds. Preferably the alkyl group is 1-25 carbon atoms. The alkyl group may optionally be substituted by one or more halogen atoms, carbonyl, hydroxyl, carboxyl, $C_1$-$C_4$-alkoxycarbonyl groups.

The term "amine" as used herein and in the claim means any basic primary, secondary or tertiary nitrogen containing group or molecule, aromatic or non-aromatic.

Throughout this specification, unless the context requires otherwise, the word "comprise", or variations such as "comprises" or "comprising", will be understood to imply the inclusion of a stated element, integer or step, or group of elements, integers or step, but not the exclusion of any other element, integer or step, or group of elements, integers or steps.

In order that the present invention may be more clearly understood, preferred forms will be described with reference to the following examples and accompanying drawings.

MODES OF CARRYING OUT THE INVENTION

Experimental Details

Fimbrolide Production

Figure 1:
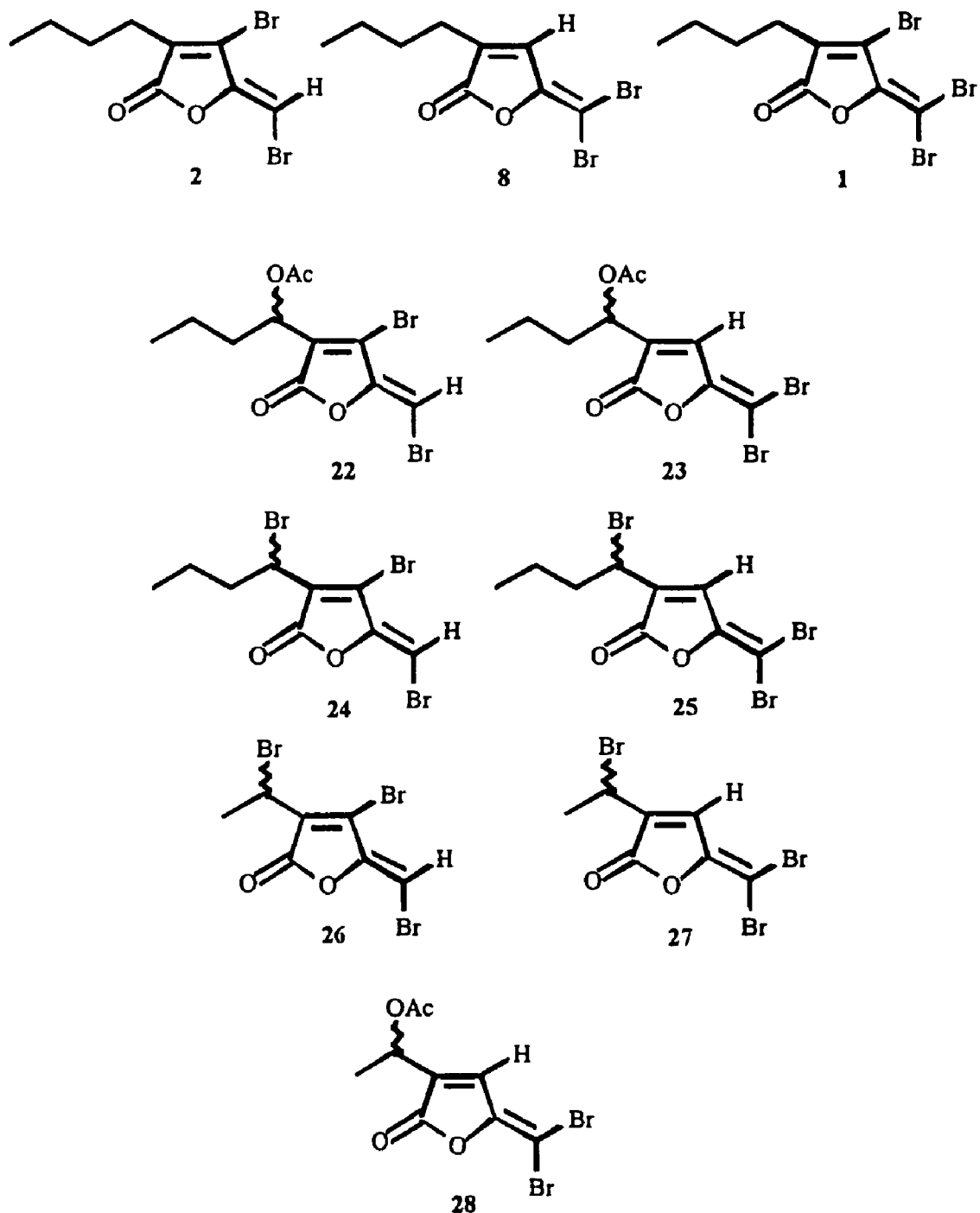
FIG. 1 shows the structure of *Delisea pulchra* furanones and synthetic analogues and derivatives tested in barnacle settlement assay.

General. Melting points are uncorrected. Microanalyses were performed by Dr H. P. Pham of The University of New South Wales Microanalytical Laboratory. $^1$H NMR spectra were obtained in $CDCl_3$ on a Bruker AC300F (300 MHz) or a Bruker DMX500 (500 MHz) spectrometer. $^{13}$C NMR were obtained in the same solvent on a Bruker AC300F (75.5 MHz) or a Bruker DMX500 (125.8 MHz) spectrometer. Chemical shifts were measured on the d scale internally referenced to the solvent peaks: $CDCl_3$ (d 7.26, d 77.04). Ultraviolet spectra were measured on an Hitachi U-3200 spectrophotometer and refer to solutions in absolute MeOH. Infrared spectra were recorded on a Perkin-Elmer 298 or a Perkin-Elmer 580B spectrophotometer and refer to paraffin mulls. The electron impact mass spectra were recorded on a VG Quattro mass spectrometer at 70 eV ionisation voltage and 200° C. ion source temperature. FAB spectra were recorded on an AutoSpecQ mass spectrometer. Column chromatography was carried out using Merck silica gel 60H (Art. 7736), whilst preparative thin layer chromatography was performed on 2 mm plates using Merck silica gel $60GF_{254}$ (Art. 7730).

Results

Fimbrolide Production

Examples of a number of fimbrolides produced are provided below.

Example 1

4-Bromo-5(bromomethylene)- and 5-(dibromomethylene)-3-(1-bromoethyl)-2(5H)-furanone N-bromosuccinimide (17.3 g, 0.097 mol) was added to a solution of 4-bromo-5-(bromomethylene)- and/or 5-(dibromomethylene)-3-ethyl-2(3H)-furanone (22.6 g, 0.08 mol) in carbon tetrachloride (500 ml) containing benzoyl peroxide (0.25 g). The mixture was irradiated with a 250 W lamp and refluxed in an oil bath for 18 h. After cooling the mixture to room temperate it was filtered and the precipitate washed with carbon tetrachloride (50 ml). The filtrate was evaporated under reduced pressure and the crude product was purified by silica gel chromatography using dichloromethane/light petroleum (2:3) as the eluent to yield the bromo compounds (22.0 g, 76%) as a 4:1 mixture.

4-Bromo-5-(bromomethylene)-3-(1-bromoethyl)-2(5H)-furanone

A pale yellow solid, m.p. 79° C. $v_{max}$ 2850, 1750, 1630, 1580, 1440, 1360, 1270, 1180, 1065, 1000, 970, 940, 1080, 755 cm$^{-1}$. $\lambda_{max}$ 306 nm (e 10826). $^1$H n.m.r. δ ($CDCl_3$) 2.06, d J 7.2 Hz, (H2')$_3$; 5.00, q, J 7.2 Hz, H1'; 6.45, s, 5-CHBr. $^{13}$C n.m.r. δ ($CDCl_3$) 22.3, C2'; 35.7, C1'; 94.3, 5-CHBr; 130.5, C4; 133.7, C; 149.5; C5; 165.8, C2. Mass spectrum: m/z 364 (M($^{81}Br_3$), 2%); 362 (M($^{81}Br_2$, $^{79}$Br), 8); 360 (M($^{81}$Br $^{79}Br_2$), 8); 358 (M($^{79}Br_3$), 2); 283 (85); 281 (100); 279 (85); 202 (12); 200 (12); 173 (18); 158 (35); 156 (35); 145 (38); 143 (42); 133 (28); 121 (26).

5-(Dibromomethylene)-3-(1-bromoethyl)-2(5H)-furanone

A white solid m.p. 119° C. $\sigma_{max}$ 2900, 1720, 1590, 1450, 1370, 1250, 1170, 1080, 1060, 1000, 960, 840, 770, 720 cm$^{-1}$. $\lambda_{max}$ 319 nm (e 12225). $^1$H n.m.r. δ ($CDCl_3$): 1.99, t, J 7.2 Hz, (H2')$_3$; 4.87, q, J 7.2 Hz, H1; 7.56, s, H4, $^{13}$C n.m.r. δ ($CDCl_3$): 23.9, C2'; 36.0, C1'; 82.8, (5-$CBr_2$); 134.7, C4; 138.2, C3; 149, C5; 165.5, C2. Mass spectrum: m/z 364 (M($^{81}Br_3$), 9%); 362 (M($^{81}Br_2$, $^{79}$Br), 18); 360 M($^{81}$Br, $^{79}$Br2), 18); 358 (M($^{79}$Br3), 9); 283 (78); 281 (100); 279 (78); 227 (8); 225 (12); 223 (8); 202 (22); 200 (32); 174 (18); 172 (44); 146 (42); 145 (50); 144 (50); 143 (60).

Example 2

3-(1-Bromobutyl)-5-(dibromomethylene)-2(5H)-furanone

The procedure described for 4-bromo-5-(bromomethylene)- and 5-(dibromomethylene)-3-(1-bromomethyl)-2 (5H)-furanone was used to treat 3-butyl-5-(dibromomethylene)-2(5H)-furanone (4.95 g, 16 mmol) with N-bromosuccinimide (3.83 g, 22 mmol) in carbon tetrachloride (70 ml) to give after chromatography the bromobutyl furanone as a yellow solid (5.48 g, 88%) m.p. 55° C. $v_{max}$ 3087, 2924, 2854, 1778, 1463, 1377, 967, 832 cm$^{-1}$. $\lambda_{max}$ 314.2 nm (e 28115). $^1$H NMR d:0.99 t, 3H, H-4'; 1.50 m, 2H, H-3', 2.10 m, 2H, H-2'; 4.72 t, 1H, H-1'; 7.54 s, 1H, H4. Mass spectrum: m/z 392 (M+1($^{81}Br_3$); 389(M+1 ($^{81}$Br, $^{79}Br_2$); 386(M+1($^{79}Br_3$); 311; 309; 307, 269; 267 (100%); 265.

Example 3

4-Bromo-5-(bromomethylene)- and 5-(dibromomethylene)-3-(1-acetoxybutyl)-2(5H)-furanone A solution of 4-bromo-5-(bromomethylene)- and/or 5-(dibromomethylene)-3-(1-bromobutyl)-2(5H)-furanone (3.00 g, 7.7 mmol) in glacial acetic acid (160 ml) containing sodium acetate (1.20 g, 15 mmol) was refluxed for 18 h. The mixture was concentrated to approximately 20 ml and neutralised with excess saturated sodium carbonate solution. The residual oil was extracted with ether (3×100 ml), washed with brine, dried over sodium sulfate and evaporated. The crude product was chromatographed on silica gel using dichloromethane/light petroleum (1:1) as eluent to yield the acetoxybutylfuranones (0.96 g, 34%) as a 4:1 mixture.

4-Bromo-5-(bromomethylene)-3-(1-acetoxybutyl)-2 (5H)-furanone

A pale yellow oil $\nu_{max}$ 2940, 1775, 1740, 1640, 1600, 1450, 1420, 1370, 1220, 1100, 1020, 985, 760, 730 cm$^{-1}$. $\lambda_{max}$ 295 nm (e 6265). $^1$H n.m.r. δ (CDCl$_3$) 0.93, t, J 7.2 Hz (H4')$_3$; 1.35, m (H3')$_2$; 1.84, m, (H2')$_2$; 2.07, s, COCH$_3$; 5.50, bt, J 7.2 Hz, H1'; 6.37, s, 5-CHBr. $^{13}$C n.m.r. δ (CDCl$_3$): 13.5, C4'; 18.5, COCH$_3$; 20.6, C3'; 33.7, C2'; 68.2, C1'; 93.5, 5-CHBr; 130.2, C4; 131.4, C3; 149.7, C5; 164.2, C2; 170.2, CO. Mass spectrum: m/z 370, (M($^{81}$Br2), <5%); 368 (M($^{81}$Br, $^{79}$Br), <5); 366, (M($^{79}$Br$_2$), <5); 327(18); 325 (26); 323 (18); 289 (22); 287 (22); 285 (14); 283 (28); 281 (14); 247 (12); 245 (12); 229 (14); 227 (14); 149 (28).

5-(Dibromomethylene)-3-(1-acetoxybutyl)-2(5H)-furanone

A pale yellow solid mp 76° C. $\nu_{max}$ 2880, 1760, 1735, 1445, 1370, 1225, 1170, 1100, 1030, 950, 840, 765, 7320 cm$^{-1}$. $\lambda_{max}$ 314 nm (e 8900).$^1$H n.m.r. δ (CDCl$_3$) 0.94, t, J 7.2 Hz (H4')$_3$; 1.36, m (H3')$_2$; 1.84, m, (H2')$_2$; 2.12, s, COCH$_3$; 5.59, bt, J 6.2 Hz, H1'; 7.39, bs, H4. $^{13}$C n.m.r. δ (CDCl$_3$): 13.6, C4'; 18.3, COCH$_3$; 20.9. C3'; 34.8, C2'; 68.3, C1'; 81.6, 5-CBr$_2$; 135.0, C4; 136.1, C3; 149.3, C5; 166.1, C2; 169.9, CO. Mass spectrum: m/z 370, (M($^{81}$Br$_2$), 28%); 368 (M($^{81}$Br, $^{79}$Br), 54); 366, (M $^{79}$Br$_2$), 28); 328 (20); 327 (18); 326 (36); 325 (28); 324 (20); 323 (18); 289 (16); 287 (16); 247 (16); 245 (16); 229 (12); 227 (12); 198 (10).

Example 4

5(Dibromomethylene)-3-(1-acetoxybutyl)-2(5H)-furanone

The procedure described for 4-bromo-5-(bromomethylene)-3-(1-acetoxybutyl)-2-(5H)-furanone was used to treat 5-(dibromomethylene)-3-(1-bromoethyl)-2(H)— furanone (2.80 g, 7.7 mmol) with sodium acetate (1.20 g, 15 mmol) in glacial acetic acid (160 ml) to give after chromatography the acetoxyethyl furanone as a white solid (0.88 g, 34%) m.p. 124° C. $\nu_{max}$ 2880, 1750, 1610, 1445, 1365, 1230, 1170, 1080, 1030, 990, 960, 930, 835, 760, 715 cm$^{-1}$. $\lambda_{max}$ 313 nm (e 31296). $^1$H n.m.r. δ (CDCl$_3$) 1.53, d, J 6.2 Hz, (H2')$_3$; 2.13, s, COCH$_3$; 5.66, m, 1H, H1'; 7.43, bs, H4. $^{13}$C n.m.r. δ (CDCl$_3$): 18.9, CH$_3$; 20.9, C2'; 53.4, C1'; 81.7, 5-CHBr; 134.6, C4; 136.7, C3; 149.2, C5; 166.0, C2; 169.6, CO. Mass spectrum: m/z 342, (M($^{81}$Br$_2$), <5%); 340 (M($^{81}$Br, $^{79}$Br), 6); 338, (M($^{79}$Br$_2$), <5); 300 (30); 299 (26); 298 (62); 297 (44); 296 (32); 295 (22); 281 (22); 279 (18); 261 (34); 259 (37); 219 (68); 217 (70); 201 (32); 200 (31); 199 (34); 174 (20); 172 (30); 170 (14); 157 (22); 145 (28); 143 (24).

Example 5

5-(Dibromomethylene)-3-(1-thioacetoxyethyl)-2 (5H)-furanone

A solution of S-(dibromomethylene)-3-(1-bromoethyl)-2 (5H)-furanone (3.00 g, 7.7 mmol) in glacial acetic acid (160 ml) containing potassium thioacetate (1.20 g, 15 mmol) was refluxed for 12 h. The mixture was concentrated to approximately 20 ml and neutralised with excess saturated sodium carbonate solution. The residual oil was extracted with ether (3×100 ml), washed with brine, dried over sodium sulfate and evaporated. The crude product was chromatographed on silica gel using dichloromethane/light petroleum (1:1) as eluent to yield the thioacetoxyethylfuranones (0.96 g, 34%) as a yellow oil $\nu_{max}$ 3200, 2910, 2850, 1780, 1730, 1690, 1600, 1450, 1420, 1380, 1350, 1270, 1170, 1105, 1010, 960, 880, 850, 810, 770 cm$^{-1}$. $\lambda_{max}$ 297 nm (e 6664). $^1$H NMR d: 1.61 (d, 3H, J 7.2 Hz, H-2'); 2.52 (s, 3H, SCOCH$_3$); 4.49 (q, 1H, J 7.2 Hz, H-1'); 7.44 (s, 1H, H4). Mass spectrum: m/z 358, (M($^{81}$Br$_2$)), 356 (M($^{81}$Br, $^{79}$Br)); 354 (M($^{79}$Br$_2$)); 316, 314, 312, 283, 281, 279, 277, 275 235, 233, 200, 172, 153, 143.

Example 6

4-Bromo-5-(bromomethylene)-3-(1-acetamidobutyl))-2(5H)-furanone

Trimethylsilyl trifluoromethanesulfonate (0.1 ml) was added with stirring to a cooled solution of 4-bromo-5-(bromomethylene)-3-(1-hydroxybutyl))-2(5H)-furanone (0.12 g, 0.37 mmol) in acetonitrile (10 ml) at 5° C. After stirring the reaction mixture at room temperature for 1 h, it was quenched with water (20 ml) and extracted with ether (3×40 ml). The combined ether extracts was washed with brine, dried over sodium sulfate and evaporated to yield the amide as a light tan oil (0.1 g, 74%). Recrystallisation of the crude product from dichloromethane/light petroleum gave the pure amide as yellow powder, m.p. 153-55° C. $^1$H n.m.r. δ (CDCl$_3$) 0.93, t, J 7.2 Hz (H4')$_3$; 1.24-1.40, m (H3')$_2$; 1.66-1.77, m, (H2')$_2$; 1.98, s, NHCOCH$_3$; 5.02, q, 7.9 Hz, H1'; 6.25, bd, J 8.7 Hz, NH; 6.38, s, 5-CHBr. $^{13}$C n.m.r. δ (CDCl$_3$): 13.5, C4'; 19.0, C3'; 23.1, NHCOCH$_3$; 35.2. C2'; 45.7, C1'; 93.6, 5-CHBr; 130.9, C4; 131.9, C3; 149.6, C5; 165.3, C2; 169.6, NHCO. Mass spectrum: m/z 369, (M($^{81}$Br$_2$), <5%); 367 (M($^{81}$Br, $^{91}$Br), <5); 365, (M($^{79}$Br$_2$), <5); 362(5); 364 (5); 326 (18); 324 (30); 322 (18); 284 (28); 282 (53); 280 (30).

Example 7

5-(Dibromomethylene)-3-(1-hydroxyethyl)-2(5H)-furanone

A solution of 5-(dibromomethylene)-3-(1-bromoethyl)-2 (5H)-furanone (18.0 g, 0.05 mol) in a mixture of dioxane (200 ml) and sulfuric acid (3M, 35 ml) was refluxed in an oil bath for 3 h. After cooling the mixture to room temperature, it was diluted with water (300 ml) and extracted with dichloromethane (3×200 ml). The combined dichloromethane extracts were washed with water, dried and evaporated. The crude product was purified by silica gel chromatography using dichloromethane/light petroleum (1:1) as an eluent to yield the hydroxyethyl furanone (9.6 g, 62%) as a white solid. m.p. 100° C. $\nu_{max}$ 3300, 2870, 1750, 1595, 1440, 1370, 1250, 1170, 1030, 985, 955, 835, 770, 720 cm$^{-1}$. $\lambda_{max}$ 311 nm (e 5832). $^1$H n.m.r δ: (CDCl$_3$), 1.50, d, J 7.2 Hz, (H2')$_3$; 4.72, m, 1H, H1', 7.49, bs, H4. $^{13}$C n.m.r. δ (CDCl$_3$): 21.8, C2'; 63.4, C1'; 81.3, 5-CHBr; 133.7, C4; 140.3, C3; 149.5, C5; 157.3, C2. Mass spectrum: m/z 300, (M+1($^{81}$Br$_2$), 18%); 298 (M+1($^{81}$Br, $^{79}$Br), 36); 296, (M+1 ($^{79}$Br$_2$), 18); 285 (22); 283 (41); 281 (28); 257 (78); 255 (100); 253 (78); 219 (15); 217 (15); 201 (22); 200 (34); 199 (36); 174 (24); 172 (38); 170 (18); 147 (21); 145 (28); 119 (38); 117 (38).

Example 8

5-(Dibromomethylene)-3-(1-hydroxbutyl)-2(5H)-furanone

The procedure described for 5-(dibromomethylene)-3-(1-hydroxyethyl)-2(5H)-furanone was used to treat 3-(1-acetoxybutyl)-5-dibromomethylene)-2(5H)— furanone (0.70 g, 1.9 mmol) with sulfuric acid (3 M, 5 ml) in dioxane (30 ml) to give after chromatography the hydroxybutyl furanone as a yellow oil (0.42 g, 68%) $v_{max}$ 3441, 2960, 2931, 2873, 1779, 1615, 1267, 1174, 1020, 965, 848 cm$^{-1}$. $\lambda_{max}$ 303.6 nm (e 1161). $^1$H NMR d: 0.95 (t, 3H, H-4'); 1.43 (m, 2H, H-3'); 1.78 (m, 2H, H-2'); 3.22 (s, 1H, OH); 4.58 (d, 1H, H-1'); 7.52 (s, 1H, H4). Mass spectrum: m/z 328, (M($^{81}$Br$_2$)), 326 (M($^{81}$Br, $^{79}$Br)); 324 (M($^{79}$Br$_2$)); 299, 297, 285, 283, (100%); 281, 257, 255, 247, 245, 203, 205, 175, 173.

Example 9

5-(Dibromomethylene)-3-(1-fluorethyl)-2(5H)-furanone

A cooled solution of 5-(dibromomethylene)-3-(1-hydroxyethyl)-2(5H)-furanone (0.47 g, 1.6 mmol) in analytical grade dichloromethane (2 ml) was added dropwise with stirring to a solution of (diethylamino)sulphur trifluoride (1 ml) in dichloromethane (2 ml) held in a dry ice/acetone cooling bath. The progress of the reaction was monitored by thin layer chromatography. Upon completion of the reaction, the mixture was added dropwise to a conical flask containing water (100 ml). The product was extracted with dichloromethane (3×50 ml) and the organic layer was dried over anhydrous sodium sulfate. The crude product was chromatographed on a silica column using dichloromethane as the eluent. The fraction with Rf of 0.90 in dichloromethane was collected and evaporated to yield the fluoro compound (0.47 g, 97%) as a yellow solid m.p. 41° C. $v_{max}$ 3096, 2924, 2854, 1790, 1754, 1609, 1463, 1376, 1264, 1192, 1092, 990, 847, 771 cm$^{-1}$. $\lambda_{max}$ 306.4 nm (e 4269). $^1$H NMR d: 1.62 (m, 3H, H-2'); 5.34, 5.52 (m, 1H, H-1'(CHF)); 7.58 (s, 1H, 5-CHBr). $^{13}$C n.m.r. δ (CDCl$_3$): 19.7 and 19.8, C2'; 82.3, CBr$_2$; 83.4 and 85.6, C1'; 134.4, C4; 136.5 and 138.5, C3; 149.2, C5; 165.7, CO. Mass spectrum: m/z 302 (M($^{81}$Br$_2$); 300 (M($^{81}$Br, $^{79}$Br); 298 (M($^{79}$Br$_2$); 202; 200; 198; 175 (100%); 172; 170.

Example 10

5-(Dibromomethylene)-3-(1-fluorobutyl)-2(5H)-furanone

The procedure described for 5-(dibromomethylene)-3-(1-fluoroethyl)-2(5H)-furanone was used to treat 5-(dibromomethylene)-3-(1-hydroxybutyl)-2(5H)-furanone (0.24 g, 0.74 mmol) with (diethylamino)sulphur trifluoride (1.0 ml in dichloromethane (3 ml) to give after chromatography the fluorobutyl furanone as a pale yellow oil (0.23 g, 97%) $v_{max}$ 3084, 2961, 2874, 1780, 1614, 1465, 1379, 1266, 1180, 1026, 966, 847, 784, 680 cm$^{-1}$. $\lambda_{max}$ 308.6 nm (e 24923). $^1$H NMR d: 0.95 (t, 3H, H-4'); 1.52, (m, 2H, H-3'); 1.88 (m, 2H, H-2'); 5.2, 5.4 (m, 1H, H-1'(CHF)); 7.56 (s, 1H, 5-CHBr). $^{13}$C n.m.r. δ (CDCl$_3$): 13.5, C4'; 17.8, C3'; 35.6 and 35.9, C2'; 82.1, 5-CBr$_2$; 86.5 and 88.8, C1'; 134.8, C4; 135.7 and 135.7 and 136.0, C3; 149.3, C5; 165.7 and 165.8, CO. Mass spectrum: m/z 330 (M(($^{81}$Br$_2$), 328 (M($^{81}$Br, $^{79}$Br); 326 (M($^{79}$Br$_2$); 288, 286, 284, 247 (100%); 207; 205.

Example 11

4-Bromo-5-(bromomethylene)-3-(1-butanoyloxybutyl))-2(5H)-furanone

4-Bromo-5-(bromomethylene)-3-(1-hydroxybutyl))-2(5H)— furanone (4.75 g. 0.015 mol) and butanoyl chloride (7.8 ml, 0.075 mol) were refluxed together for 7 h then cooled and poured into water (50 ml) and extracted with ether (3×30 ml). The combined ether extracts were washed sequentially with saturated sodium bicarbonate (2×50 ml) and brine (50 ml), dried over sodium sulfate, and evaporated. The crude product was purified by silica gel chromatography using ether/light petroleum (1:9) as the eluent to yield the butanoyloxybutyl furanone as a pale yellow oil (3.60 g, 60%) $v_{max}$ 2950, 1780, 1730, 1635, 1600, 1450, 1380, 1280, 1240, 1165, 1060, 980, 770 cm$^{-1}$. $\lambda_{max}$ 289 nm (e 14900). $^1$H n.m.r δ (CDCl$_3$) 0.91, t, J 7.4 Hz OCOCH$_2$CH$_2$CH$_3$; 0.93, t, J 7.2 Hz, (H4')$_3$; 1.35, m (H3')$_2$; 1.66, q, J 7.4 Hz, OCOCH$_2$CH$_2$CH$_3$; 1.80-1.95, m, (H2')$_2$; 2.32, t, J 7.4 Hz, OCOCH$_2$CH$_2$CH$_3$; 5.50, dd, J 6.4 Hz 8.0 Hz, H1'; 6.36, s, 5-CHBr. $^{13}$C n.m.r. δ (CDCl$_3$): 13.4, OCOCH$_2$CH$_2$CH$_3$; 13.5, C4'; 18.2, OCOCH$_2$CH$_2$CH$_3$; 18.4, C3'; 33.5, C2'; 35.7, OCOCH$_2$CH$_2$CH$_3$; 68.0, C1'; 93.2, 5-CHBr; 130.6, C4; 132.4, C3; 149.6, C5; 165.9, C2; 172.7, CO. Mass spectrum: m/z 399, (M+1($^{81}$Br$_2$), <5%); 397 (M+1($^{81}$Br, $^{79}$Br);<5); 395, (M+1(79Br$_2$)<5); 327 (18); 325 (28); 323 (18); 317 (26); 315 (26); 311 (8); 309 (16); 307 (8); 283 (16); 281 (34); 279 (16); 267 (42); 265 (40); 247 (16); 245 (16); 223 (56); 221 (44).

Example 12

4-Bromo-5-(bromomethylene)-3-(1-octadecanoyloxybutyl))-2(5H)-furanone

4-Bromo-5-(bromomethylene)-3-(1-hydroxybutyl))-2(5H)-furanone (0.24 g, 0.7 mmol) and octadecanoyl chloride (0.3 ml, prepared by octadecanoic acid and thionyl chloride) were stirred in an oil bath at 110° C. for 24 h. The reaction mixture was diluted with ether (50 ml) and washed with water (3×20 ml) followed by brine (30 ml). The organic phase was dried over sodium sulfate and evaporated to yield a brown oil. The crude product was purified by silica gel chromatography using dichloromethane as the eluent to yield the octadecanoyloxybutyl furanone as dark tan oil (0.14 g, 32%). $^1$H n.m.r δ (CDCl$_3$) 0.87, t, J 7.2 Hz, OCO(CH$_2$)$_{16}$CH$_3$; 0.95, t, J 7.2 Hz, (H4')$_3$; 1.28, m, OCOCH$_2$(CH$_2$)$_{15}$CH$_3$; 1.35-1.45, m, (H3')$_2$; 1.58-1.60, m, OCOCH$_2$CH$_2$; 1.75-2.05, m, (H2')$_2$; 2.34, t, J 7.2 Hz, OCOCH$_2$(CH$_2$)$_{15}$CH$_3$; 5.43, dd, J 6.2 Hz 7.7 Hz, H1'; 6.37, s, 5-CHBr. $^{13}$C n.m.r. δ (CDCl$_3$): 13.5, OCO(CH$_2$)$_{16}$CH$_3$; 14.1, C4'; 18.6, 22.7, 24.8, 29.2, 29.3, 29.4, 29.6, 29.7, 31.9, 33.8, 33.9, CH$_2$; 68.0, C1'; 93.3, 5-CHBr; 130.7, C4; 131.3, C3; 149.8, C5; 163.7, C2; 173.1, CO.

Example 13

Method A

4-Bromo-5-(bromomethylene)-3-(1-acryloyloxybutyl)-2(5H)-furanone

The procedure described for 4-bromo-5-(bromomethylene)-3-(1-butanoyloxybutyl))-2(5H)-furanone was used to treat 4-bromo-5-(bromomethylene)-3-(1-hydroxybutyl))-2(5H)-furanone (4.75 g, 0.015 mol) with acryloyl chloride (6.0 ml, 0.073 mol). The crude product was purified by silica gel chromatography using either/light petroleum (1:9) as the eluent to yield the acryloyloxybutyl furanone as a pale yellow oil (3.60 g, 60%). $v_{max}$ 3060, 2940, 2850, 1770, 1710, 1620, 1590, 1430, 1390, 1385, 1280, 1250, 1160, 1095, 1030, 970, 835, 795, 760, 700 cm$^{-1}$. $\lambda_{max}$ 289 nm (e 18170). $^1$H n.m.r. δ (CDCl$_3$) 0.91, t J 7.4 Hz, ester CH$_3$; 0.97, t, J 7.4 Hz, (H4')$_3$; 1.38, m, (H3')$_2$; 1.84-2.04, m, (H2')$_2$; 5.63, dd, J 6.7 Hz 8.2 Hz, H1'; 5.88, d, J 10.7 Hz, CH=CH$_2$; 6.14, dd, J 10.7 Hz 16.3 Hz, CH=CH$_2$; 6.39, s, 5-CHBr; 6.46, d, J 16.3 Hz, CH=CH$_2$. $^{13}$C n.m.r. δ (CDCl$_3$): 13.5, C4'; 18.5, C3'; 33.7, C2', 68.2, C1'; 93.5, 5-CHBr; 127.5; CH=CH$_2$; 130.4, C4; 131.5, CH=CH2; 132.1, C3; 149.8, C5, 163.7, C2; 165.2, CO. Mass spectrum: m/z 382, (M($^{81}$Br$_2$), <5%); 380 (M($^{81}$Br, $^{79}$Br), <5); 378, (M($^{79}$Br$_2$), <5); 327 (14); 325 (28); 323 (14); 301 (16); 299 (16); 283 (8); 281 (12); 279 (8); 269 (12); 267 (24); 265 (12); 229 (18); 227 (24); 225 (18); 223 (20); 203 (34); 201 (46); 175 (32); 173 (48); 147 (38); 145 (46) 143 (48).

Method B

Concentrated sulfeuric acid (1 drop) was added to a solution of 4-bromo-5-(bromomethylene)-3-(1-hydroxybutyl))-2(5H)-furanone (0.94 g, 3.0 mmol) and acrylic acid (2 ml) in benzene (5 ml). The mixture was refluxed for 4 h, and after cooling to room temperature, poured into water (50 ml). The crude product was extracted with ether (2×50 ml), and the combined ether extract washed with sodium carbonate solution. The extract was dried over anhydrous sodium sulfate, evaporated and chromatographed over silica column using dichloromethane/light petroleum as the eluent to yield the pure acryloyloxybutyl fluranone as a tan oil (0.48 g, 42%).

Example 14

4-Bromo-5-(bromomethylene)-3-(1-butanoyl)-2(5H)-furanone

To an ice cooled situation of 4-bromo-5-(bromomethylene)-3-(1-hydroxybutyl)-2(5H)-furanone (2.77 g, 8.5 mmol) in acetone (75 ml) was added dropwise with stirring Jones reagent (12 ml, prepared by dissolving chromium trioxide (13.36 g) in sulfuric acid (11.2 ml) and water (38.5 ml). The mixture was stirred at room temperature for 1 h and the progress of the reaction monitored by thin layer chromatography. After the completion of the reaction, the mixture was poured into water (200 ml) and extracted with ether (3×100 ml). The combined ether extracts were washed with brine (100 ml), dried over sodium sulfate and evaporated to yield the crude ketone (2.23 g, 81%) as a yellow solid. Recrystallisation of the crude ketone from dichloromethane/hexane gave the pure ketone as yellow plates, m.p. 83-84° C. $v_{max}$ 1700, 1680, 1630, 1540, 1310, 1000 cm$^{-1}$. $^1$H n.m.r. δ (CDCl$_3$) 0.97, t, J 7.2 Hz, (H4')$_3$; 1.70, m, (H3')$_2$; 2.93, t, J 7.2 Hz, (H2')$_2$; 6.74, s, 5-CHBr. $^{13}$C n.m.r. δ (CDCl$_3$): 13.6, C4'; 16.7, C3'; 44.4, C2'; 99.3, 5-CHBr; 125.7, C4; 138.1, C3; 150.4, C5; 163.5, CO; 194.1, C1'. Mass spectrum: m/z 326, (M($^{81}$Br$_2$), <5%); 324 (M($^{81}$Br, $^{79}$Br), 5); 320, (M($^{79}$Br$_2$), <5); 298 (10); 296 (22); 281 (16); 279 (8); 225 (4); 131 (14); 77 (32); 71 (52); 43 (100).

Covalently Bound Furanone Polymer Synthesis

Example 15

Preparation of Furanone Acrylate Homopolymer

A mixture of 4-bromo-5-(bromomethylene)- and 5-(dibromomethylene)-3-(1-acryloyloxybutyl)-2(5H)-furanone (0.36 g), AIBN (0.003 g) and toluene (0.75 ml) was degassed and then heated at 60° C. for 24 h. Hexane was added to the mixture and the precipitated polymer was washed once with methanol. The final product was collected and dried to yield the polymer (0.04 g, 11% conversion) of average mass 14284.

Example 16

Preparation of Furanone Acrylate-Polymethyl Methacrylate Copolymer

A mixture of methyl methacrylate (3.0 g), 4-bromo-5-(bromomethylene)- and 5-(dibromomethylene)-3-(1-acryloyloxybutyl)-2(5H)-furanone (0.75 g) and AIBN (0.006 g) was degassed for ½ h by purging with nitrogen gas and then heated at 60° C. for 24 h. Hexane (50 ml) was added to the mixture and the precipitated polymer was washed once with methanol. The polymer was further purified by reprecipitation from chloroform and excess methanol. The final produce was collected and dried to yield the polymer (1.74 g, 47% conversion) of average mass 7578.

Example 17

Preparation of Furanone Acrylate-Polystyrene Copolymer

A mixture of styrene (15 g), 4-bromo-5-(bromomethylene)- and 5-(dibromomethylene)-3-(1-bromoethyl)-2(5H)-furanone (0.16 g) and AIBN (0.023 g) was degassed for ½ h by purging with nitrogen gas and then heated at 60° C. for 3 h. After the completion of polymerisation, the mixture was poured into hexane and the precipitated polymer was washed twice with ether and dried in vacuo (0.1 mm Hg) at 40° C. for 24 h to yield the polymer (12.9 g, 85% conversion). An XPS analysis of the powered polymer in aluminium foil confirmed the presence of bromine.

Example 18

Preparation of Furanone Acrylate-Poly(Styrene/MEMA/MMA) Polymer

To a solution of styrene (5 g), MMA (5 g) and HEMA (5 g) in toluene (8 ml) was added 4-Bromo-5-(bromomethylene)- and 5-(dibromomethylene)-3-(1-bromoethyl)-2(5H)-furanone (0.15 g) followed by dodecanethiol (2 ml) and AIBN (0.4 g). The mixture was degassed by two freeze-thaw cycles and then heated at 70° C. for 24 h. After the completion of polymerisation, the mixture was treated with hexane and the precipitated polymer was washed with hexane and dried in vacuo (0.1 mm Hg) at room temperature for 24 h to yield the polymer (22.2 g, 87% conversion).

Example 19

4-Bromo-5-(bromomethylene)-3-(1-butenyl)-2(5H)-furanone

Concentrated sulfuric acid (2 drops) was added to a solution of 4-Bromo-5-(bromomethylene)-3-(1-hydroxybutyl)-2(5H)-furanone (2.0 g) in toluene (10 ml). The mixture was refluxed for 4 h, and after cooling to room temperature, poured into water (50 ml). The crude product was extracted with ether (2×50 ml), and combined ether extract washed with sodium carbonate solution. The extract was dried over sodium sulfate, evaporated and chromatographed over silica column using light petroleum as the eluent to yield the pure 3-)(1-1-butenyl)-furanone as a light yellow oil (0.40 g). $^1$Hnmr d (CCl$_3$) 1.10, t, J 7.2H$_z$, (H4')$_3$; 2.26, q, J 7.2H$_z$, (H3')$_2$; 6.20, d, CH=CH; 7.20, d, CH=CH, 6.24, s, 5-CHBr.

Fimbrolide Biological Activity

MATERIALS AND METHODS

Inhibition of Cyprid Settlement

The effects of synthetic furanones on the settlement of barnacle larvae were tested using cyprids of the cosmopolitan fouling barnacle *Balanus amphitrite* Darwin. The naturally occurring furanone 2, and the synthetically prepared compounds 281 (a 1:1:1 mixture of synthesised 2 & 8 & 1), 2223 (a 1:1 mixture of synthesised 22 & 23), 2425 (a 1:1 mixture of synthesised 24 & 25), 26, 27 and 28 (FIG. 1) were compared for their efficacy in deterring barnacle cyprid settlement. Compounds were dissolved in ethanol (99.7%+ purity) at a concentration of 180 µg.ml$^{-1}$ to 1.8 µg.ml$^{-1}$. A 0.5 ml aliquot of each compound to be tested was added to treatment petri dishes (surface area 9 cm$^2$), and 0.5 ml of ethanol only was added to ethanol control dishes. Dishes were dried on a shaker resulting in a coating of extract on treatment dishes with a concentration range of 10 µg.cm$^{-2}$ to 100 µg.cm$^{-2}$ for each compound.

Cypris larvae were obtained from laboratory cultures of adult brood stock of *Balanus amphitrite*. Nauplii of *B. amphitrite* were collected and reared on *Skeletonema costatum* until reaching cyprid stage. Cypris larvae were filtered and maintained in filtered seawater at 5° C. for five days prior to use in settlement assays (Rittschof et al., 1992).

Settlement tests were conduced by adding 25-35 cyprids to either treatment dishes, ethanol control dishes, or untreated dishes, each containing 4 ml of sterilised filtered seawater (0.22 µm). All the treatments and controls were tested in triplicate. Test dishes were incubated for 24 h at 28° C. in a 15:9 h light-dark cycle (Rittschof et al., 1992). After 24 h, the test was terminated by the addition of three drops of 40% formaldehyde, and non-settled larvate filtered from the dish. The percent settlement of cyprids was then determined by counting settled and non-settled larvae.

Statistical Analyses

The data from the bioassays were analysed by analysis of variance (ANOVA) followed by Tukey's multiple comparison test. Data were analysed as percentages after arcsin Äp transformations.

Results

Inhibition of Cyprid Settlement

Figure 2:
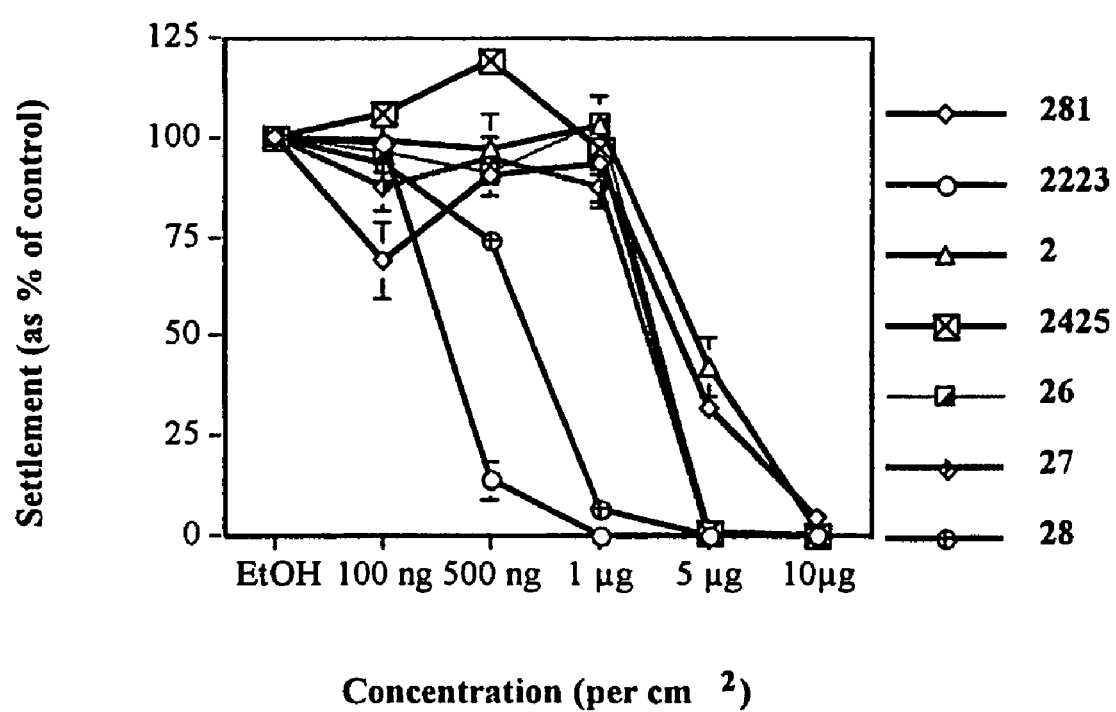
FIG. 2 shows the effect of furanones 2, 281, 2223, 2425, 26, 27 and 28 on the settlement of barnacle cyprid larvae as measured by settlement expressed as a percent of the control.

The settlement of *Balanus amphitrite* Cypris larvae was significantly inhibited by the compounds tested (FIG. 2; two-factor ANOVA [metabolite×concentration] followed by Tukey's test). All treatments completely inhibited settlement at the highest concentration (10 µg.cm$^{-2}$). Ethanol controls were used in the analysis as ethanol had no significant effect on settlement (single factor ANOVA, P=0.17). The synthetic furanone 2223 (FIG. 1) was the most active metabolites (FIG. 2). At a concentration of 1 µg.cm$^{-2}$ 2223 completely inhibited settlement and inhibited settlement by 80% compared to the control at 500 ng.cm$^{-2}$. The next most inhibitory compound was the furanone 28 (FIG. 1) which inhibited settlement completely at 5 µg.cm$^{-2}$ and inhibited settlement by 90% at 1 µg.cm$^{-2}$. A group of furanones, 2425, 26 and 27 completely inhibited settlement at 5 µg.cm$^{-2}$ but had no effect at 1 µg.cm$^{-2}$. The furanone 2 and the synthetic analogue 281, a 1:1:1 mixture of 2, 8 and 1 (FIG. 1) were the least effective compounds completely inhibiting settlement at 10 µg.cm$^{-2}$.

Inhibition of *Staphylococcus aureus*

*Staphylococcus aureus* is a facultatively anaerobic, non-motile, gram-positive coccus and is normally associated with the skin, skin glands, and mucous membranes of humans. *S. aureus* is the most important human staphylococcal pathogen and causes, for example, boils, abscesses and wound infections.

A screening experiment of the different furanones against the growth of *S. aureus* was performed in a BioRad 3550 Microplate reader. The growth was measured as absorbance at 610 nm up to 9 h. A complex growth media, Nutrient Broth, was used and the cells were grown at 37° C. Both natural furanones (compounds 2, 3 and 4) and synthesised furanones (compounds 33/34 and 45) were used in the experiment at the concentration 10 µg/ml.

Figure 3:
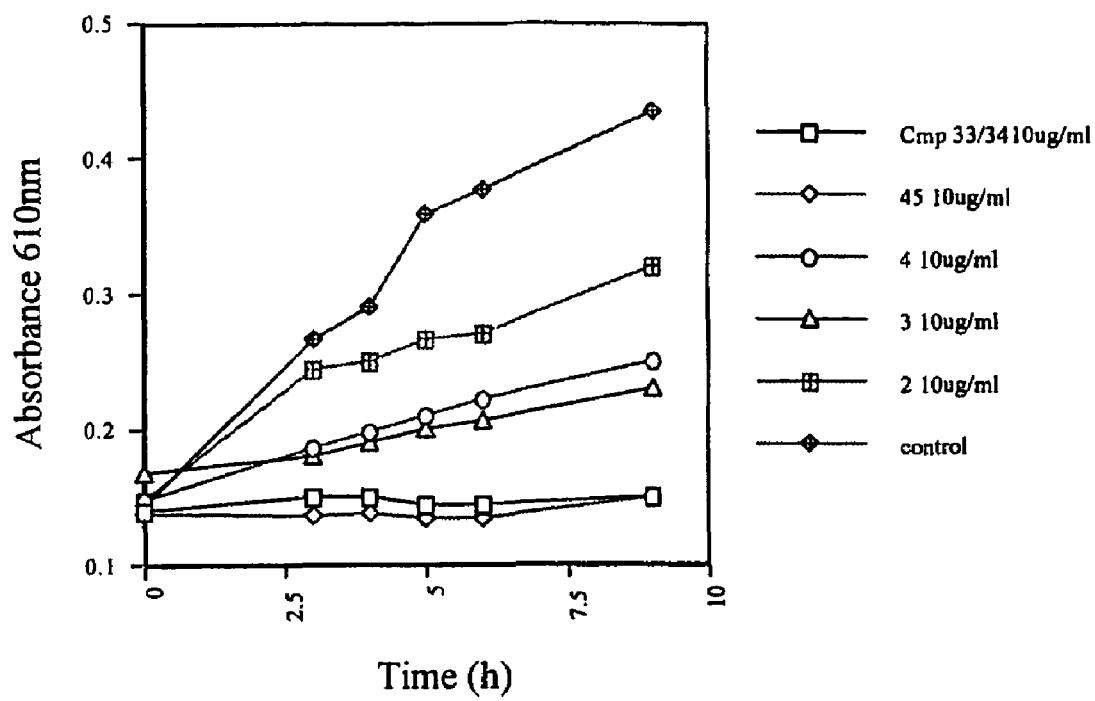
FIG. 3 shows growth curves of *Staphylococcus aureus* against different furanones.

The results showed that the synthesised furanones (33/34 and 45) inhibited growth of *S. aureus* more effectively than the natural furanones (FIG. 3). The growth of the cells inoculated with 33/34 and 45 was completely inhibited for 9 h compared to 2 h for those inoculated with the natural compounds. All furanones, however, inhibited the growth of *S. aureus* compared to the control.

Further experiments were performed with the synthesised furanones 45 and 33/34 at the concentration 10 µg/ml and 5 µg/ml. The cells were grown in side arm flasks in NB media at 37° C. The growth of the cells were measured at 610 nm for up to 48 h.

Figure 4:
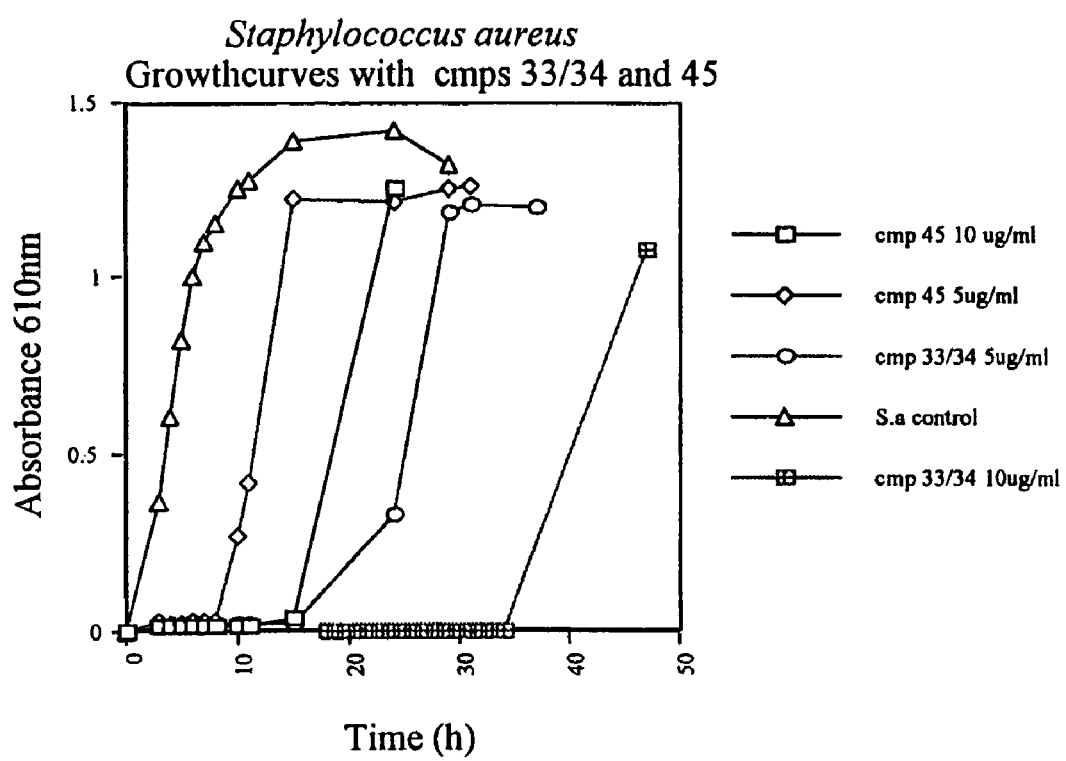
FIG. 4 shows growth curves of *Staphylococcus aureus* against compounds 33/34 and 45.
Figure 5:
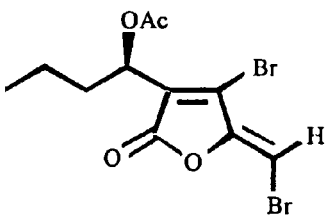
FIGS. 5-5I show the structural formulae for other specific examples of compounds in accordance with the present invention.
Figure 5:
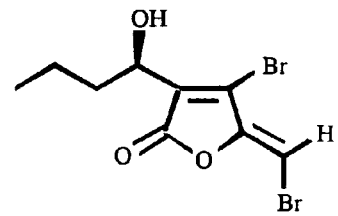
Figure 5:
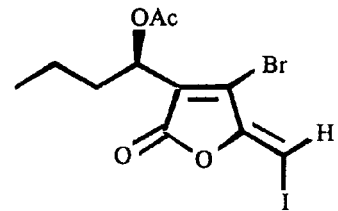
Figure 5A:
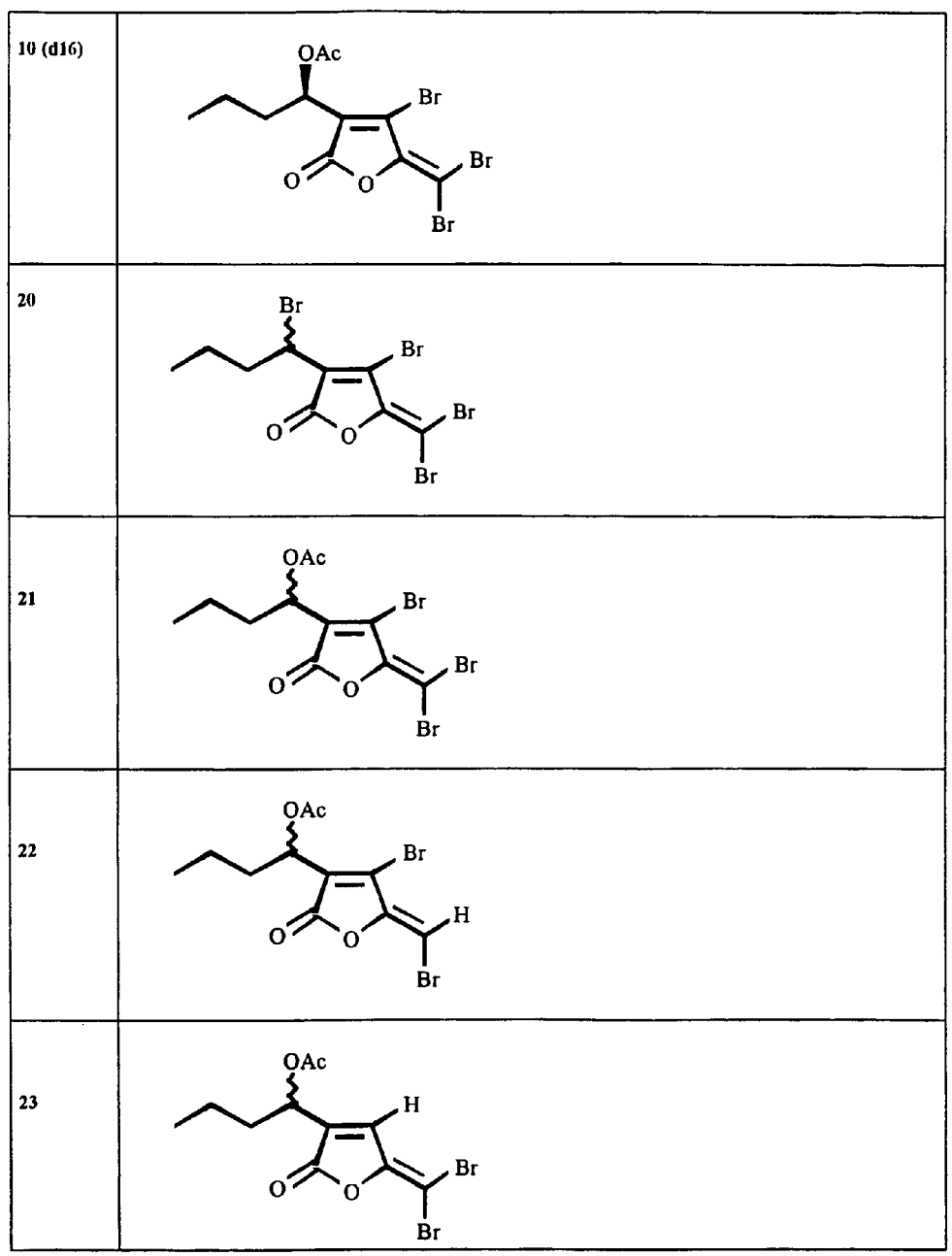
Figure 5B:
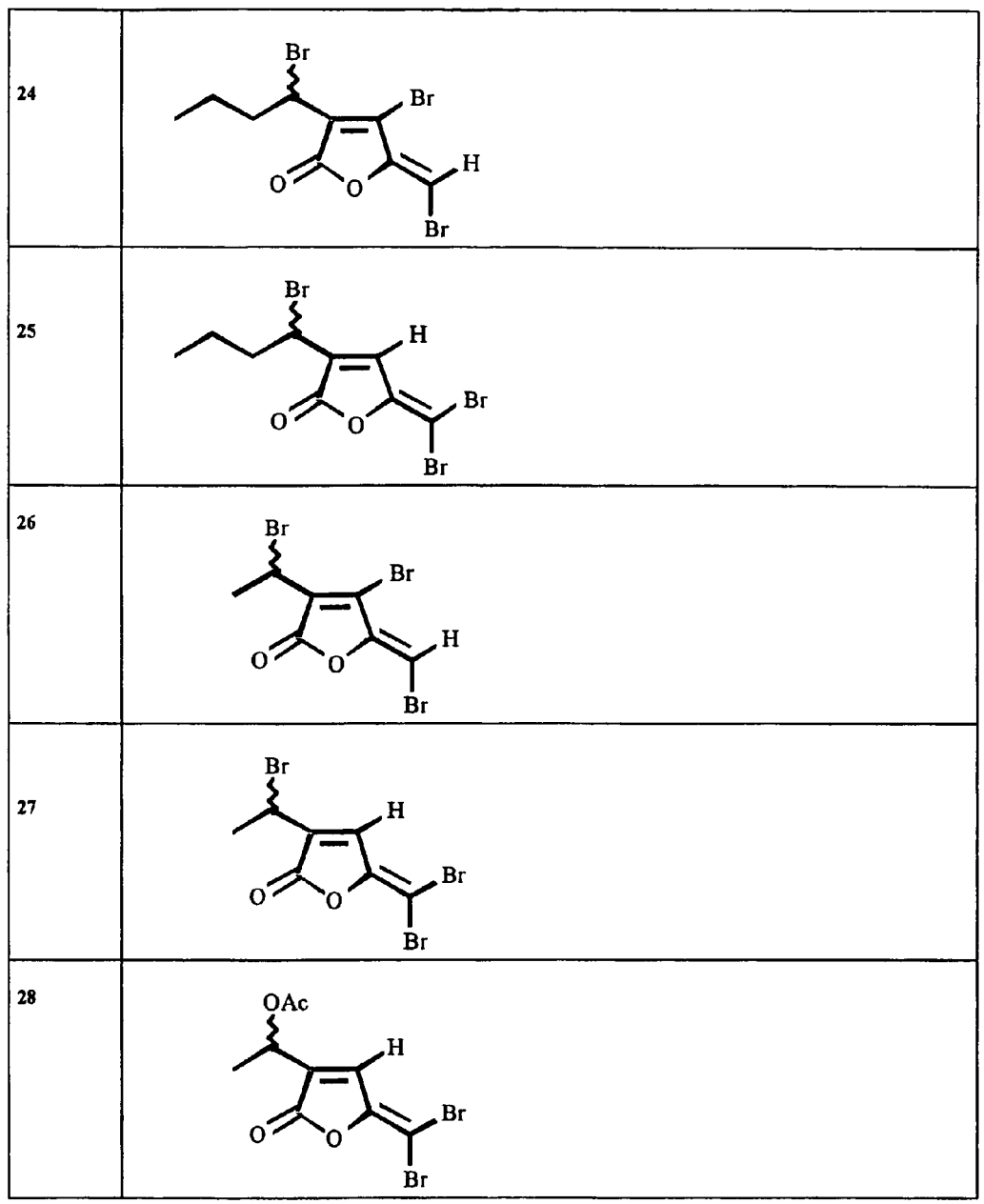
Figure 5C:
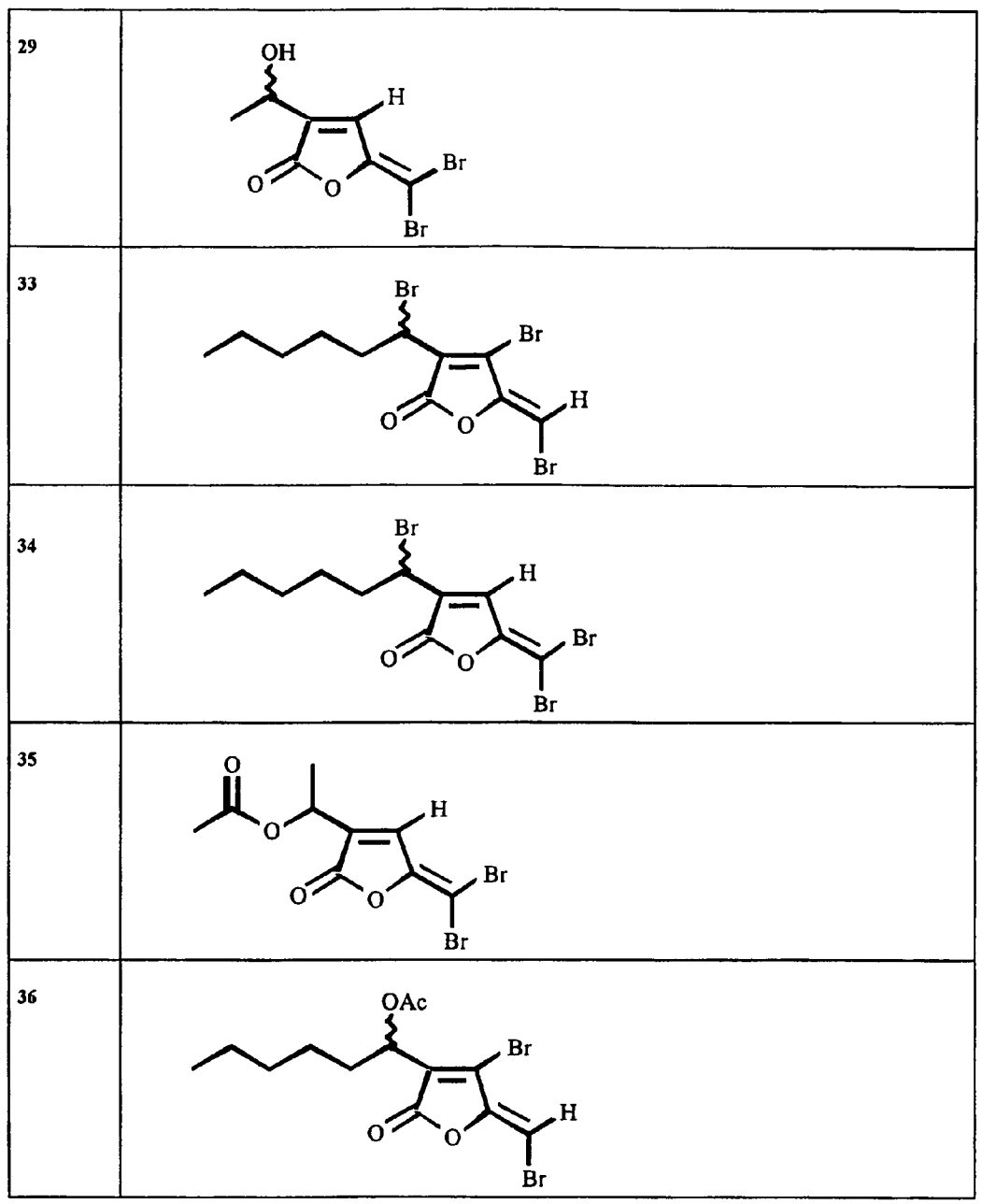
Figure 5D:
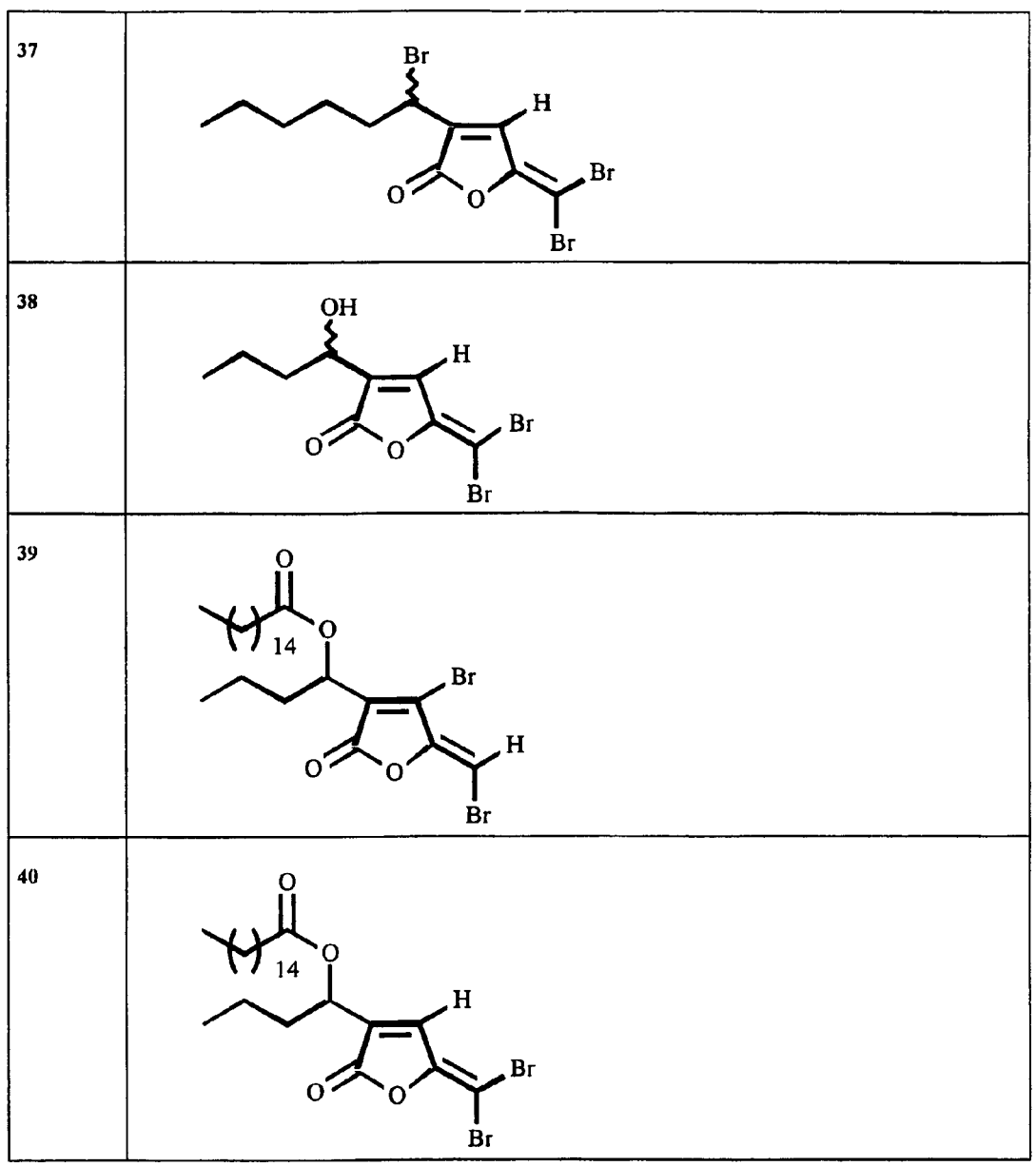
Figure 5E:
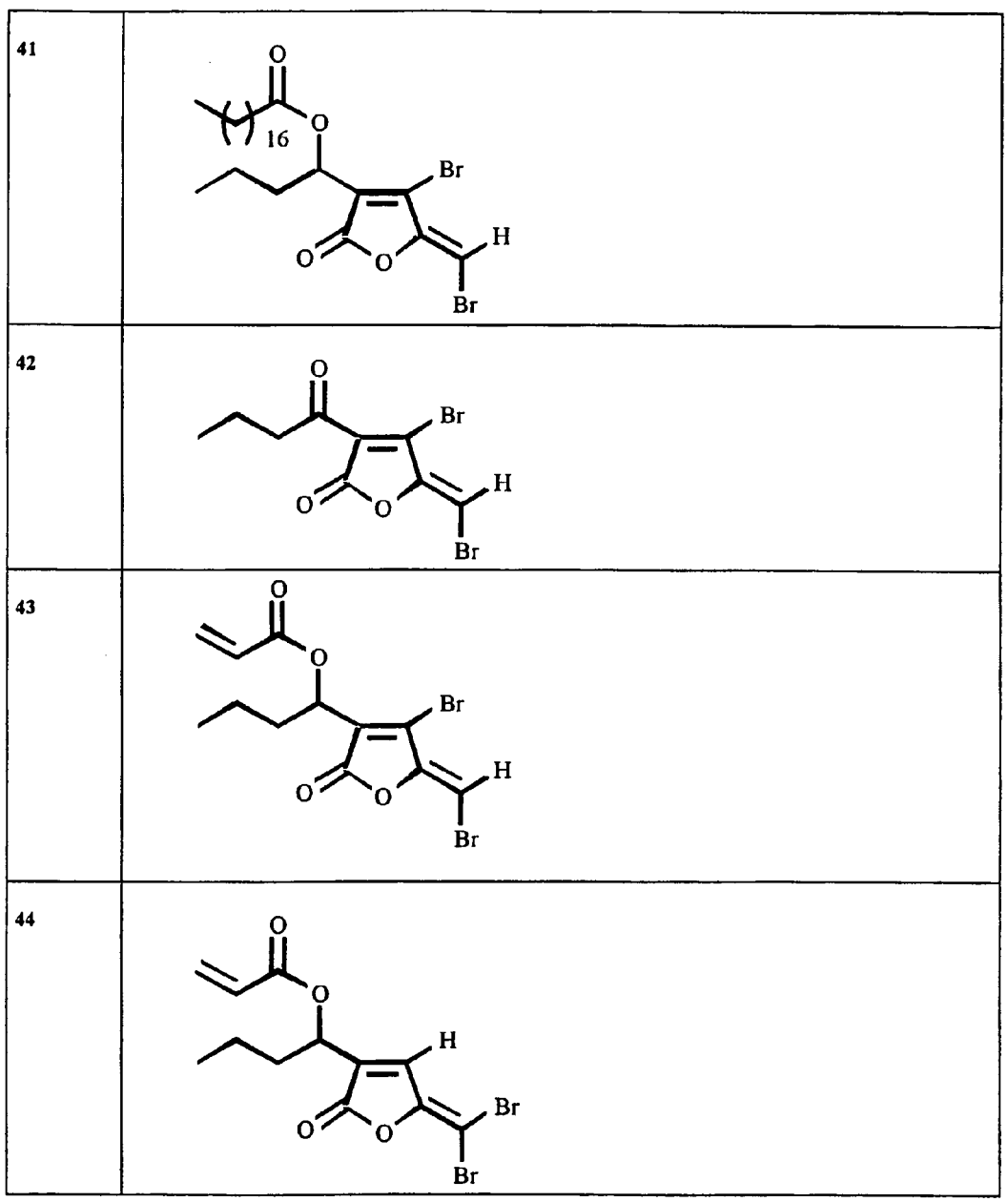
Figure 5F:
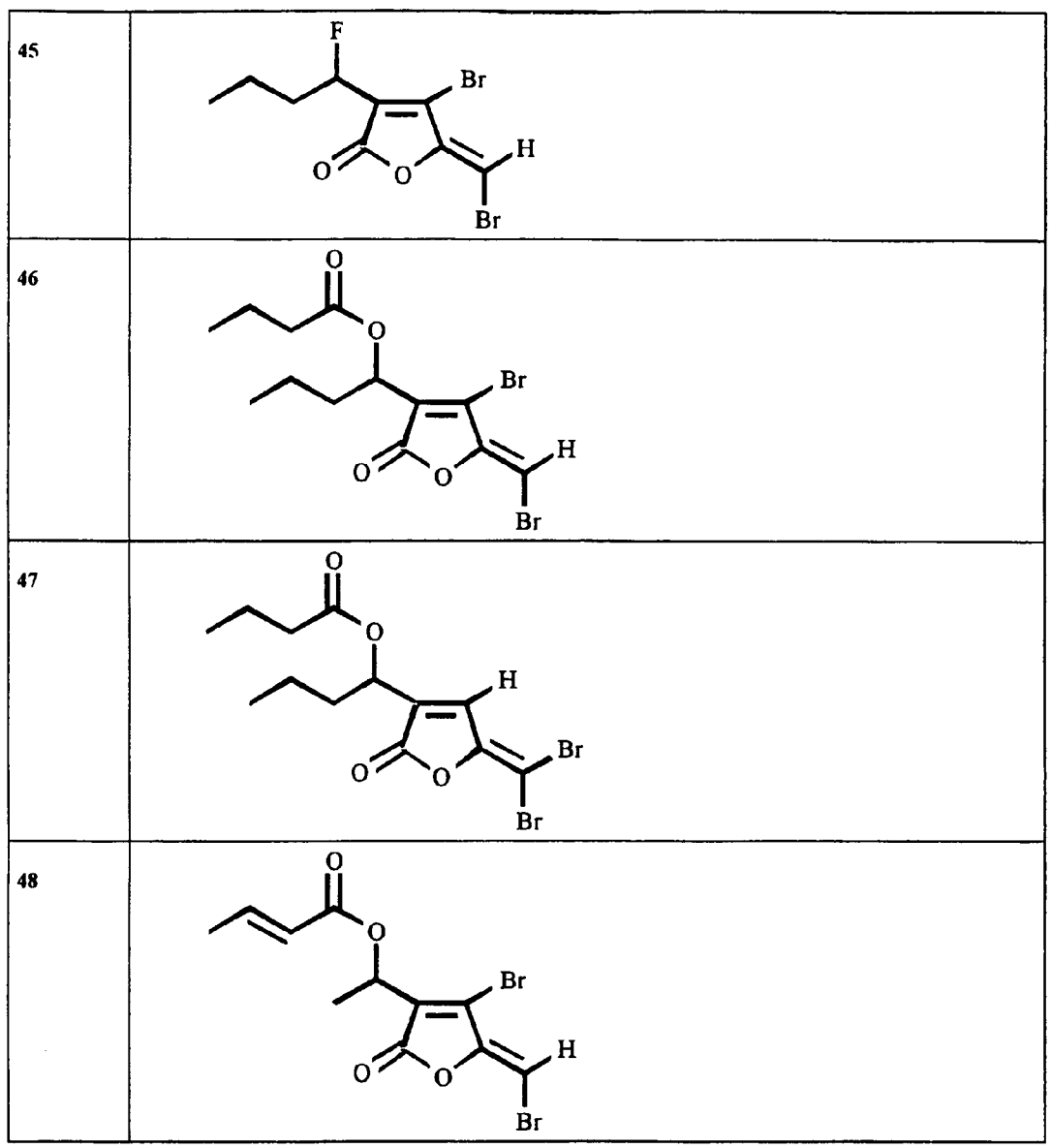
Figure 5G:
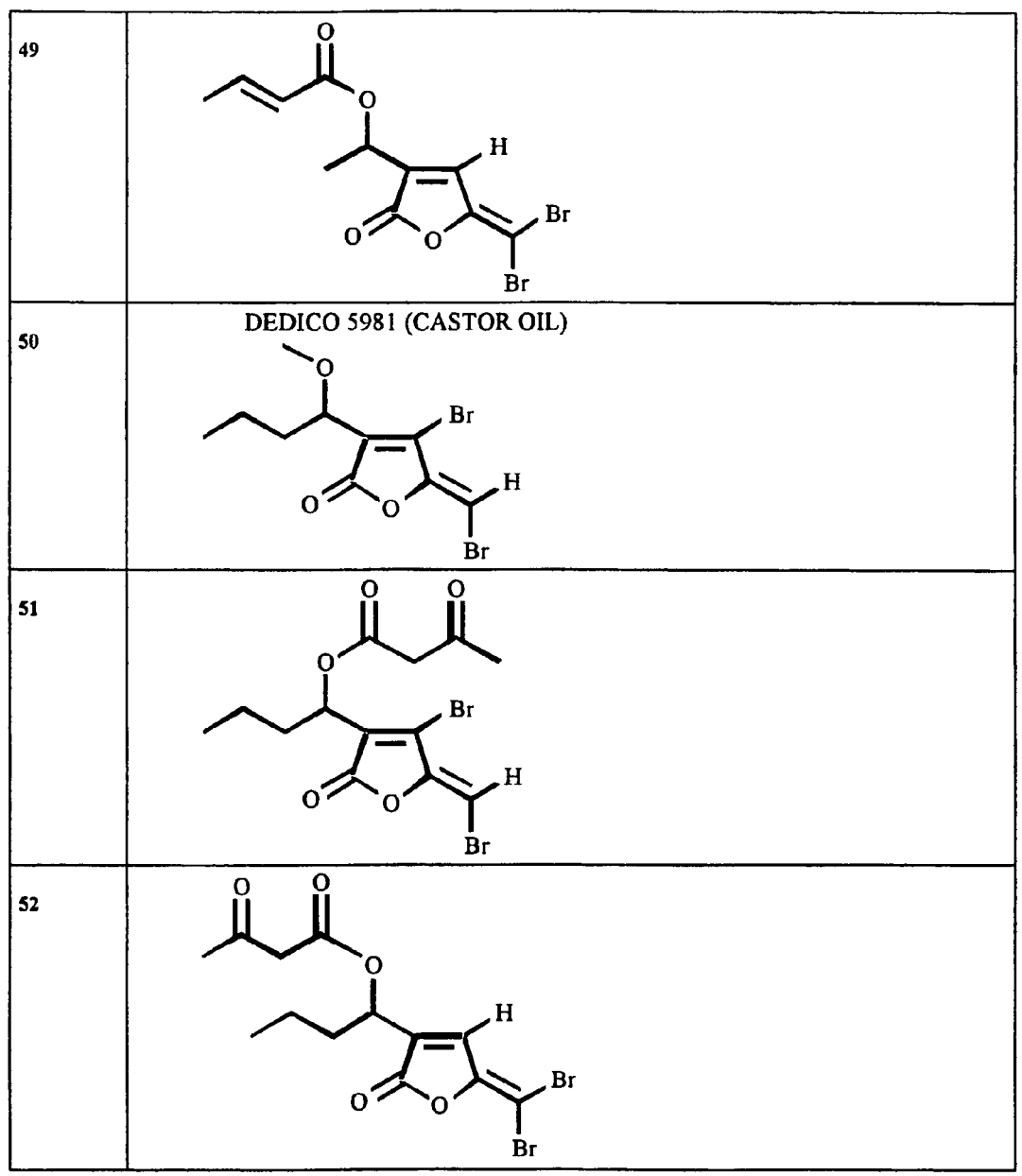
Figure 5H:
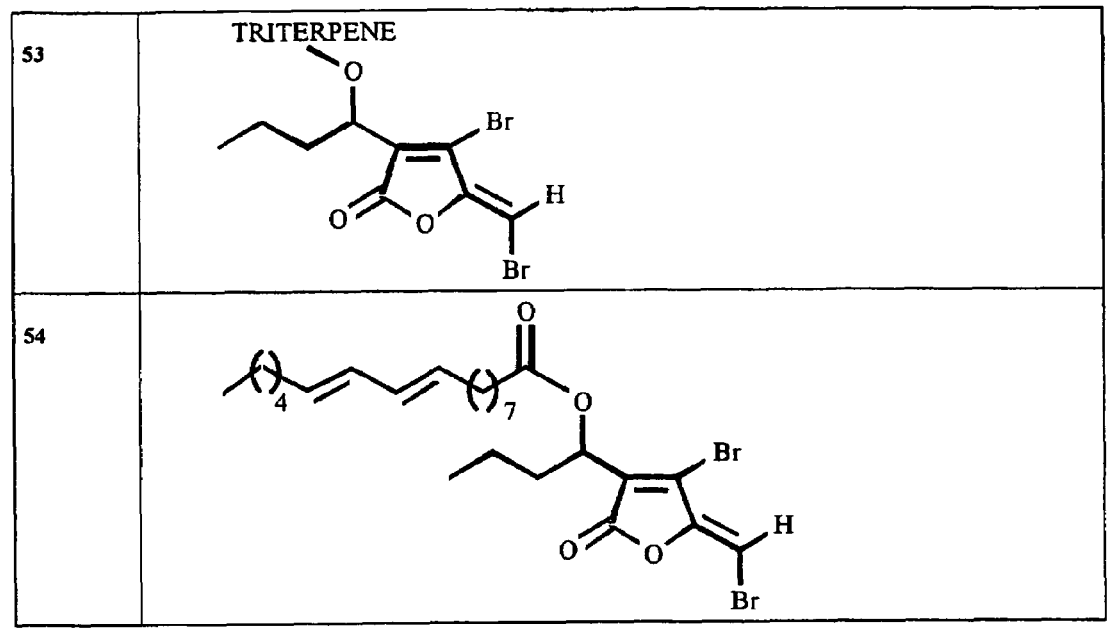
Figure 5I:
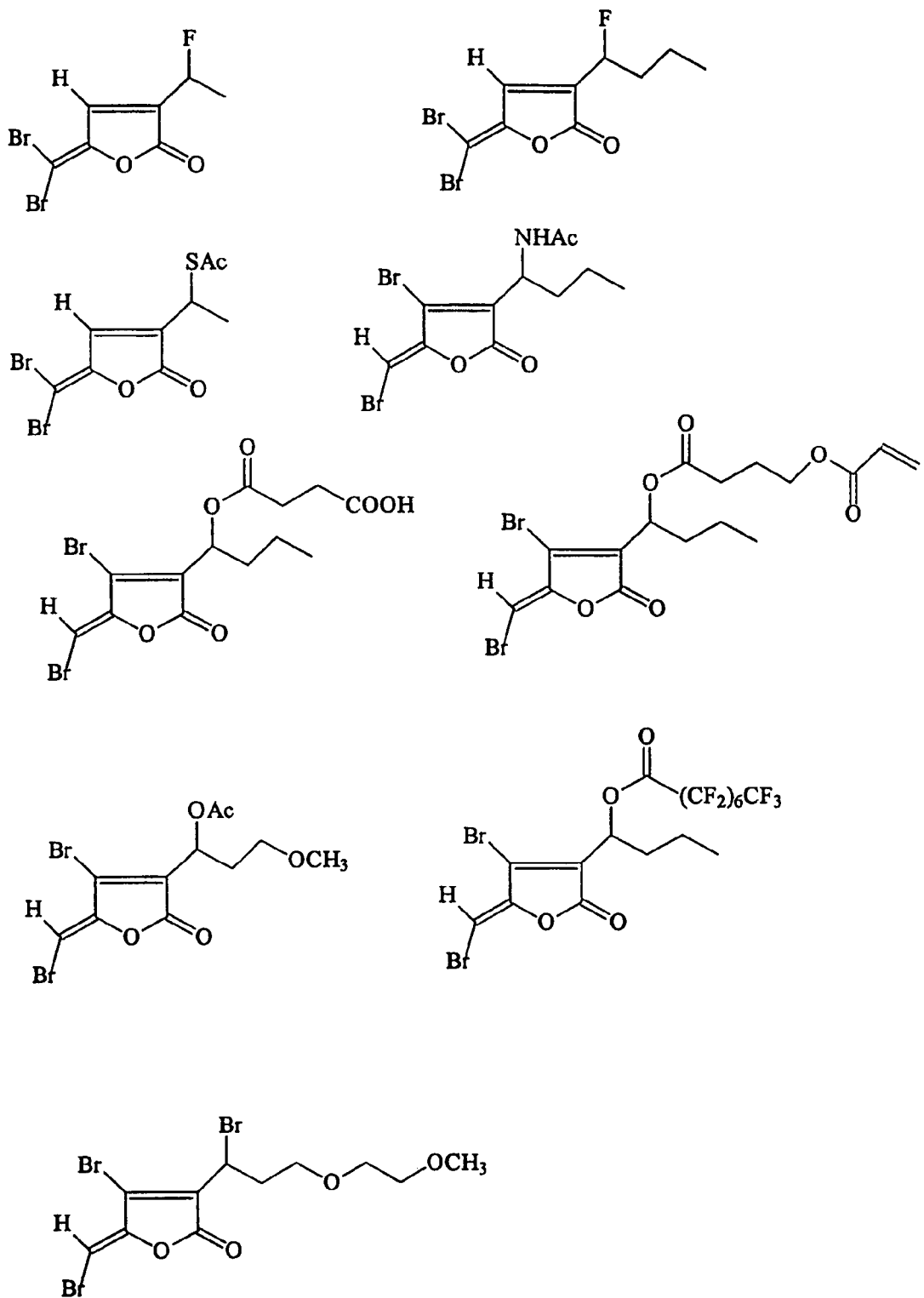

The results showed that compound 33/34 was more effective at inhibiting growth of *S. aureus* compared to compound 45 (FIG. 4), however, both compounds at both concentrations inhibited the growth completely for 9 h. Growth of the cells occurred after 9 h with compound 45 at the concentration 5 µg/ml and after 15 h at the concentration 10 µg/ml Compound 33/34 at 5 µg/ml inhibited the growth for 15 h and at the concentration 10 µg/ml the growth of *S aureus* was completely inhibited for 34 h.

Discussion

The derivatisation of naturally occurring furanones resulted in an increase in the deterrence of barnacle settlement. For example, manipulation of the length of the acyl side chain and the functionality on the 1' position of the acyl side chain of the furanone resulted in a significant increase in activity. The is clearly demonstrated in a comparison of the activity of furanones 2 and 2425. In 2425 a bromine has been added in the 1' position of acyl chain resulting in a five fold increase in activity in the settlement bioassay (FIG. 2). All of the synthesised furanones are either novel compounds not being previously reported in the literature or are racemic mixtures of a naturally occurring furanone. The racemic analogues of the naturally occurring compounds have the same activity as the naturally occurring optically pure form. Therefore, the synthetic furanones, both analogues of naturally occurring compounds and novel compounds, have activity comparable to or better than the compounds from which their structure was derived, e.g. furanone 2 vs 2425.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A compound according to formula (Ia):

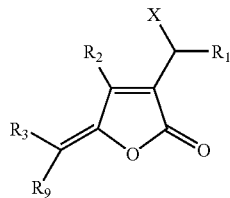

(Ia)

wherein $R_1$ is hydrogen, alkyl, alkoxy, oxoalkyl, alkenyl, aryl or arylalkyl;

X is halogen, OH, OC(O)$R_1$, alkoxy, alkenyloxy, aryloxy, or arylalkyloxy;

$R_2$ is hydrogen;

$R_3$ and $R_9$ are each halogen; and wherein each substituent can be straight chain or branched chain and wherein each alkyl is optionally substituted by one or more fluorine, bromine, iodine, carboxyl, $C_1$-$C_4$-alkoxycarbonyl, hydroxyl, carbonyl and aryl groups; and provided that the compound is not

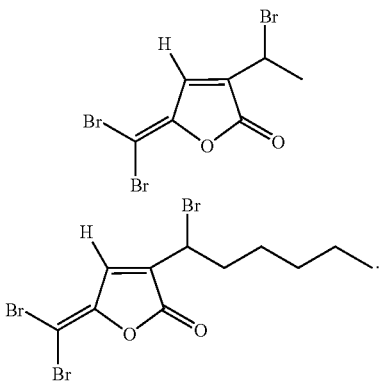

2. A compound according to claim 1, wherein X is F, Cl, I, OH, OC(O)$R_1$, alkoxy, alkenyloxy, aryloxy, or arylalkyloxy.

3. A compound according to claim 1 or claim 2, wherein X is OH, OC(O)$R_1$, alkoxy, alkenyloxy, aryloxy, or arylalkyloxy.

* * * * *